United States Patent
Day et al.

(10) Patent No.: US 9,809,621 B2
(45) Date of Patent: Nov. 7, 2017

(54) STABLE PEPTIDE-BASED PACE4 INHIBITORS

(75) Inventors: Robert Day, Sherbrooke (CA); Witold A. Neugebauer, Ottawa (CA); Yves Dory, Cookshire (CA)

(73) Assignee: SOCPRA SCIENCES SANTÉ ET HUMAINES S.E.C., Sherbrooke (CA)

( * ) Notice: Subject to any disclaimer, the term of this patent is extended or adjusted under 35 U.S.C. 154(b) by 487 days.

(21) Appl. No.: 14/342,041

(22) PCT Filed: Aug. 30, 2012

(86) PCT No.: PCT/CA2012/050601
§ 371 (c)(1),
(2), (4) Date: Mar. 18, 2014

(87) PCT Pub. No.: WO2013/029180
PCT Pub. Date: Mar. 7, 2013

(65) Prior Publication Data
US 2014/0206622 A1    Jul. 24, 2014

Related U.S. Application Data

(60) Provisional application No. 61/530,478, filed on Sep. 2, 2011.

(51) Int. Cl.
| | | |
|---|---|---|
| *A61K 38/00* | (2006.01) | |
| *C07K 9/00* | (2006.01) | |
| *C07K 7/06* | (2006.01) | |
| *A61K 47/48* | (2006.01) | |
| *A61K 38/08* | (2006.01) | |
| *A61K 45/06* | (2006.01) | |

(52) U.S. Cl.
CPC ............... *C07K 7/06* (2013.01); *A61K 38/08* (2013.01); *A61K 45/06* (2013.01); *A61K 47/48038* (2013.01); *A61K 47/48215* (2013.01); *A61K 38/00* (2013.01)

(58) Field of Classification Search
None
See application file for complete search history.

(56) References Cited

FOREIGN PATENT DOCUMENTS

| WO | 2005/025611 | 3/2005 |
|---|---|---|
| WO | WO2010/003231 A1 * | 7/2009 |
| WO | WO 2010/003231 | 1/2010 |
| WO | WO 2010003231 A1 * | 1/2010 |

OTHER PUBLICATIONS

Becker, et al., J Med Chem. 53(3):1067-75, 2010.
Couture, et al., BioMol Concepts. 2(5):421-38, 2011.
International Preliminary Report on Patentability in International Application No. PCT/CA2012/050601 dated Mar. 4, 2014.
International Search Report and Written Opinion in International Application No. PCT/CA2012/050601 dated Nov. 30, 2012.
Fugere et al. "Short polybasic peptide sequences are potent inhibitors of PC5", Molecular Pharmacology, vol. 71, No. 1, 2007, pp. 323-332.
Levesque et al. "The Multi-Leu peptide inhibitor discriminates between PACE4 and furin and exhibits antiproliferative effects on prostate cancer", Journal of Medicinal Chemistry, 2012.

* cited by examiner

*Primary Examiner* — Jeanette Lieb
(74) *Attorney, Agent, or Firm* — Norton Rose Fulbright

(57) ABSTRACT

It is provided PACE4 inhibitors and their uses for treating infection, cancer. Particularly, it is provided a method or use for the treatment of a cancer in a subject, comprising administering to the subject a therapeutically effective amount of the PACE4 inhibitors or the composition disclosed.

11 Claims, 9 Drawing Sheets

MULTI-LEU PEPTIDE
Ac-LLLLRVKR-NH2

ARGININE ANALOGS 4-amidinobenzylamide [AMBA]   4-aminobut-2-en-1-yl guanidine [ΔR-CO2]   azaβ3-arginine [azaβ3R]

LEUCINE ANALOGS azaβ3-leucine [azaβ3L]   D-leucine [DLeu]   Click peptidic bound [click]   Norleucine [Nleu]   Conjugated Double-bonded amino acid [c-ene]   Unconjugated Double-bonded amino acid [uc-ene]

[DLeu]$^{P8}$-ML

[DLeu]$^{P8}$-ML-[AMBA]$^{P1}$

STABLE PEPTIDE-BASED PACE4 INHIBITORS

CROSS-REFERENCE TO RELATED APPLICATIONS

The present application is a national phase application under 35 U.S.C. §371 of International Application No. PCT/CA2012/050601 filed Aug. 30, 2012, which claims benefit of U.S. Provisional Application No. 61/530,478, filed Sep. 2, 2011, both of which are hereby incorporated herein by reference in their entirety.

TECHNICAL FIELD

The present description relates to PACE4 inhibitors and their stable analogues.

BACKGROUND

Pro-protein convertases (PCs) are serine proteases that optimally cleave substrates at R-X-K/R-R motif. These processing events, resulting in the activation of protein precursors, occur at multiple levels of cell secretory pathways, and even at the cell surface.

In mammalian cells, seven members of this family have been identified that cleaves at paired basic residues: furin, PACE4, PC1/3, PC2, PC4, PC5/6 and PC7, with differential expression in tissues, ranging from ubiquitous (eg. furin) to an endocrine restricted expression (PC1/3 and PC2).

In addition to normal cell functions, PCs, are implicated in many pathogenic states, because they process to maturity membrane fusion proteins and pro-toxins of a variety of bacteria and viruses, including anthrax, botulinum toxins, influenza A $H_5N_1$ (bird flu), flaviviruses, Marburg and Ebola viruses (Thomas, 2002, Nat. Rev. Mol. Cell. Biol., 3: 753-766). After processing by PCs and the subsequent endocytic internalization in the complex with the respective cell surface receptor followed by acidification of the endosomal compartment, the processed, partially denatured, infectious proteins expose their membrane-penetrating peptide region and escape into the cytoplasm (Collier and Young, 2003, Annu. Rev. Cell Dev. Biol., 19: 45-70). Pathogens or their toxins, including influenza virus, *Pseudomonas*, and anthrax toxins, require processing by host proprotein convertases (PCs) to enter host cells and to cause disease.

Cancer cells are characterized by multiple genetic alterations that confer physiological changes, leading to uncontrolled division and ability to invade other tissues. These acquired capabilities, namely self-sufficiency in growth signals, insensitivity to growth-inhibitory signals, evasion of programmed cell death, limitless replicative potential, sustained angiogenesis, tissue invasion and metastasis are essential for malignant growth. Recent studies have associated PCs to cancer (Bassi et al., 2005, Mol. Carcinog., 44: 151-161; Khatib et al., 2002, Am. J. Pathol., 160: 1921-1935).

The association of PCs with cancer was firstly done by comparative studies of normal and cancerous cells showing higher expression of PCs in small cell lung cancer (Clark et al., 1993, Peptides, 14: 1021-1028), non-small cell lung carcinoma (Mbikay et al., 1997, Cancer, 75: 1509-1514), breast (Cheng et al., 1997, Int. J. Cancer, 71: 966-971), colon (Tzimas et al., 2005, BMC Cancer, 5: 149), and head and neck (Bassi et al., Mol. Carcinog., 31: 224-232) tumors cells. A correlation between expression of some PCs, namely furin and PACE4, and tumor cell aggressiveness has been established for different cell types. It as been demonstrated that the overexpression of PACE4 in non-malignant keratinocyte cell lines renders these cells malignant. Non-selective inhibitors that target several PCs together (such as furin, PACE4 and PC5/6 together) have been described (Bassi et al., 2005, Cancer Res., 65: 7310-7319; Mahloogi et al., 2002, Carcinogenesis, 23: 565-572; Bassi et al., 2000, Mol. Carcinog., 28: 63-69; Hubbard et al., 1997, Cancer Res., 57: 5226-5231).

Moreover, it has been proposed that PC activity regulates epithelial cell differentiation in a prostate cancer cell line. One possible mechanism underlying these observations could be on the basis of the precursors activation by overexpressed PCs. Thus, it is hypothesized that aberrant processing events provide cancer cells a higher capacity to (i) remodel the extracellular; (ii) to interact with their host micro-environment to favor tumor cell adhesion and; (iii) to modulate their proliferation and differentiation. Alternatively, PC's overexpression is required to sustain these pathophysiological functions to maintain cancer cells immortality.

The situation becomes more complex as the expression/activity of PCs is modulated differently in various cancer cells or cancer models. If one wishes to understand the specific contribution of each PC in tumorigenesis, the necessity for potent, specific and cell effective inhibitors, either pharmacologic or molecular, for each member of this enzyme family is crucial. Until now, these pharmacological tools are limited and lack specificity for single PCs.

PCT application publication No. WO 2010/003231, which is hereby incorporated by reference in its entirety, discloses PACE4 inhibitors and their uses for limiting proliferation of cells.

There is still a need to be provided with improved PCs inhibitors and particularly PACE4 inhibitors. It would be highly desirable to be provided with more stable and selective PACE4 inhibitors that are effective in treating cancer.

SUMMARY

One aim of the present description is to provide PACE4 inhibitors and their uses for treating cancer.

It is provided a peptide sequence comprising the following formula I:

$$Z\text{-}Xaa_5\text{-}Xaa_7\text{-}Xaa_6\text{-}Xaa_5\text{-}Arg_4\text{-}Xaa_3\text{-}Xaa_2\text{-}Arg_1\text{-}Xaa_1 \quad (I)$$

wherein $Xaa_{1'}$ is absent or arginine, an analogue or mimic of arginine or stereoisomer thereof;

$Arg_1$ and $Arg_4$ are independently arginine, analogue or mimic of arginine or stereoisomer thereof;

$Xaa_2$ is a basic amino acid, an analogue or stereoisomer thereof;

$Xaa_3$ is any amino acids, an analogue or stereoisomer thereof;

$Xaa_5$, $Xaa_6$, $Xaa_7$ and $Xaa_8$ independently are Leu, His, Arg, Ser, an analogue or stereoisomer thereof; and Z comprises at least one of acetyl, azido and PEG group, fatty acids, steroids derivatives and sugars linked to the N-terminal of the peptide sequence;

with the proviso that $Xaa_5$, $Xaa_6$, $Xaa_7$ and $Xaa_5$ are not aromatic or negatively charged amino acids.

The term "analogues" is intended to mean analogues of amino acids and pseudo peptide bonds, such as "click", aza, -ene (double conjugated or unconjugated C=C bonds).

The linked sugar can be mono or poly sugar.

In a particular embodiment, the N terminus of the inhibitor is acylated (e.g. acetylated). Further, the N terminus acylation is with fatty omega amino acids or with steroid derivatives.

The fatty (saturated or unsaturated) omega amino acids can be C2 to C18, more preferably the fatty omega amino acids are selected from the group consisting of 11-amino undecanoic acid or 8-amino octanoic acid.

According to another aspect of the present description, there is provided a composition comprising the PACE4 inhibitors as defined herein and a carrier.

In another embodiment, the composition further comprises at least one anti-cancer drug.

"Concurrent administration" and "concurrently administering" as used herein includes administering a composition as described herein and an anti-cancer drug compound in admixture, such as, for example, in a pharmaceutical composition, or as separate formulation, such as, for example, separate pharmaceutical compositions administered consecutively, simultaneously, or at different times.

Preferably, the composition is adapted for delivery by at least one of the following route selected from the group consisting of oral, mucosal, intranasal, intraocular, intratracheal, intrabronchial, intrapleural, intraperitoneal, intracranial, intramuscular, intravenous, intraarterial, intralymphatic, subcutaneous, intratumoral, gastric, enteral, colonic, rectal, urethral and intravesical route.

According to still another aspect of the present invention, there is provided a method of lowering PACE4 activity in a cell, comprising contacting the PACE4 inhibitors or the composition as defined herein with the cell, thereby lowering PACE4 activity in the cell.

According to yet another aspect of the present description, there is provided a method of reducing the proliferation of a cell in a subject, comprising administering the PACE4 inhibitors or the composition as defined herein to the subject, thereby reducing the proliferation of the cell in the subject.

According to a further aspect of the present description, there is provided a method of reducing tumor growth in a subject, comprising administering the PACE4 inhibitors or the composition as defined herein to the subject, thereby reducing tumor growth in the subject.

According to yet a further aspect of the present description, there is provided a method for the treatment of a cancer, in a subject, comprising administering to said subject a therapeutically effective amount of the PACE4 inhibitors or the composition as defined herein, thereby treating cancer in the subject.

Preferably, the cell is in a subject. More preferably, the cell is a cancer cell. More preferably, the cell has increased PACE4 activity.

According to still a further aspect of the present description, there is provided the use of the PACE4 inhibitors or the composition as defined herein in the manufacture of a medicament for treating cancer in a subject.

More specifically, the cancer is a prostate cancer or a metastasis thereof.

More particularly, the cancer encompassed herein is breast cancer, glioma, large intestinal cancer, lung cancer, small cell lung cancer, stomach cancer, liver cancer, blood cancer, bone cancer, pancreatic cancer, skin cancer, head or neck cancer, cutaneous or intraocular melanoma, uterine sarcoma, ovarian cancer, rectal or colorectal cancer, anal cancer, colon cancer, fallopian tube carcinoma, endometrial carcinoma, cervical cancer, vulval cancer, squamous cell carcinoma, vaginal carcinoma, Hodgkin's disease, non-Hodgkin's lymphoma, esophageal cancer, small intestine cancer, endocrine cancer, thyroid cancer, parathyroid cancer, adrenal cancer, soft tissue tumor, urethral cancer, penile cancer, prostate cancer, chronic or acute leukemia, lymphocytic lymphoma, bladder cancer, kidney cancer, ureter cancer, renal cell carcinoma, renal pelvic carcinoma, CNS tumor, glioma, astrocytoma, glioblastoma multiforme, primary CNS lymphoma, bone marrow tumor, brain stem nerve gliomas, pituitary adenoma, uveal melanoma, testicular cancer, oral cancer, pharyngeal cancer, pediatric neoplasms, leukemia, neuroblastoma, retinoblastoma, glioma, rhabdomyoblastoma or sarcoma.

In an alternate embodiment, the composition can be formulated for concurrent administration during a suitable anti-cancer therapy, such as a surgical procedure, chemotherapy, hormonal therapy and localization radiation.

According to yet another aspect of the present description, there is provided the use of the PACE4 inhibitors or the composition as defined herein for lowering PACE4 activity in a cell, for reducing proliferation of a cell in a subject, and for reducing tumor growth in a subject.

In a particular embodiment, the inhibitor or the composition reduces cell proliferation, tumor growth or metastasis formation.

The terms used herein are explained below. Each term, alone or in combination with another term, means as follows.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or lower alkyl groups such as methyl, ethyl or propyl, are attached to a linear alkyl chain. "Lower alkyl" means a group having about 1 to about 6 carbon atoms in the chain which may be straight or branched. Non-limiting examples of suitable alkyl groups include methyl, ethyl, n-propyl, isopropyl and t-butyl.

The terms "alkenyl" represent a linear, branched or cyclic aliphatic hydrocarbon group which may be straight or branched and comprising about 1 to about 20 carbon atoms and has one or more double bonds in the chain.

"Alkylene" means a difunctional group obtained by removal of a hydrogen atom from an alkyl group that is defined above. Non-limiting examples of alkylene include methylene, ethylene and propylene.

"Aryl" means an aromatic monocyclic or multicyclic ring system comprising about 6 to about 14 carbon atoms, preferably about 6 to about 10 carbon atoms. Examples include but are not limited to phenyl, tolyl, dimethylphenyl, fluorenyl, aminophenyl, anilinyl, naphthyl, anthryl, phenanthryl or biphenyl.

"Arylene" means a difunctional group obtained by removal of a hydrogen atom from an aryl group that is defined above. Examples include but are not limited to phenylene, tolylene, dimethylphenylene, fluorene, aminophenylene, anilinylene, naphthylene, anthrylene, phenanthrylene or biphenylene.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination.

The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

"Heteroarylene" means a difunctional group obtained by removal of a hydrogen atom from a heteroaryl group that is defined above. Non-limiting examples of pyridylene, pyrazinylene, furanylene, thienylene and pyrimidinylene.

The term "arylalkylene" represents an aryl group attached to the adjacent atom by an alkylene.

The term "arylalkenylene" represents an aryl group attached to the adjacent atom by an alkenylene.

The term "NR1-alkylene" represents a NR1 group attached to an alkylene.

The term "NR1-alkenylene" represents a NR1 group attached to an alkenylene.

The term "NR1-arylene" represents a NR1 group attached to an arylene.

The term "NR1-heteroarylene" represents a NR1 group attached to an heteroarylene.

The term "NR1-arylalkylene" represents a NR1 group attached to an arylalkylene.

The term "NR1-arylalkenylene" represents a NR1 group attached to an arylalkenylene.

The term "alkylene-NR2" represents an alkylene attached to the adjacent atom by a NR2 group.

The term "alkenylene-NR2" represents an alkenylene attached to the adjacent atom by a NR2 group.

The term "arylene-NR2" represents an arylene attached to the adjacent atom by a NR2 group.

The term "heteroarylene-NR2" represents an heteroarylene attached to the adjacent atom by a NR2 group.

The term "arylalkylene-NR2" represents an arylalkylene attached to the adjacent atom by a NR2 group.

The term "arylalkenylene-NR2" represents an arylalkenylene attached to the adjacent atom by a NR2 group.

The term "NR1-alkylene-NR2" represents a NR1 group attached to an alkylene, the alkylene is attached to the adjacent atom by a NR2 group.

The term "NR1-alkenylene-NR2" represents a NR1 group attached to an alkenylene, the alkenylene is attached to the adjacent atom by a NR2 group.

The term "NR1-arylene-NR2" represents a NR1 group attached to an arylene, the arylene is attached to the adjacent atom by a NR2 group.

The term "NR1-heteroarylene-NR2" represents a NR1 group attached to an heteroarylene, the heteroarylene is attached to the adjacent atom by a NR2 group.

The term "NR1-arylalkylene-NR2" represents a NR1 group attached to an arylalkylene, the arylalkylene is attached to the adjacent atom by a NR2 group.

The term "NR1-arylalkenylene-NR2" represents a NR1 group attached to an arylalkenylene, the arylalkenylene is attached to the adjacent atom by a NR2 group.

The terms "alkylene-COOH", "alkenylene-COOH", "arylene-COOH", "heteroarylene-COOH", "arylalkylene-COOH", "heteroarylalkylene-COOH" or "alkenyl-COOH" represents an alkylene, an alkenylene, an arylene, an heteroarylene, an arylalkylene, an heteroarylalkylene or an alkenyl attached to the adjacent atom by a —COOH group.

The term "independently" means that a substituent can be the same or a different definition for each item.

"PEG" means a polyethylene glycol prepared through polymerization of ethylene oxide that are commercially available, and can include a wide range of molecular weights from 300 g/mol to 10,000,000 g/mol.

BRIEF DESCRIPTION OF THE DRAWINGS

Having thus generally described the nature of the invention, reference will now be made to the accompanying drawings.

DETAILED DESCRIPTION

It is provided herein PACE4 inhibitors and their uses for treating cancer.

PACE4 has been proposed as having a role and consequently has representing a new therapeutic target in lung tumours (Mbikay et al., 1997, Br J Cancer, 75: 1509-1514), breast cancer (Cheng et al., 1997, In J Cancer, 11: 966-971; Lapierre et al., 2007, Cancer Res, 67: 9030-9034), conversion of squamous cell carcinoma (SCC) to a more advanced malignant spindle cell carcinoma (SPCC) (Hubbard et al., 1997, Cancer Res, 57: 5226-5231), colorectal cancer (Khatib et al., 2001, J Biol Chem, 276: 30686-30693), ovarian cancer (Fu et al., 2003, Mol Cancer Res, 1: 569-576) and in general mechanisms underlying tumor cell invasion and tumor progression (Bassi et al., 2000, Mol Carnog, 28: 63-69; Mahloogi et al., 2002, Carcinogenesis, 23: 565-572; Bassi et al., 2005, Cancer Res, 65: 7310-7319; Yuasa et al., 2007, Gene, 402: 103-110; and Bassi et al., 2010, Neoplasia, 12: 516-526).

Figure 1:
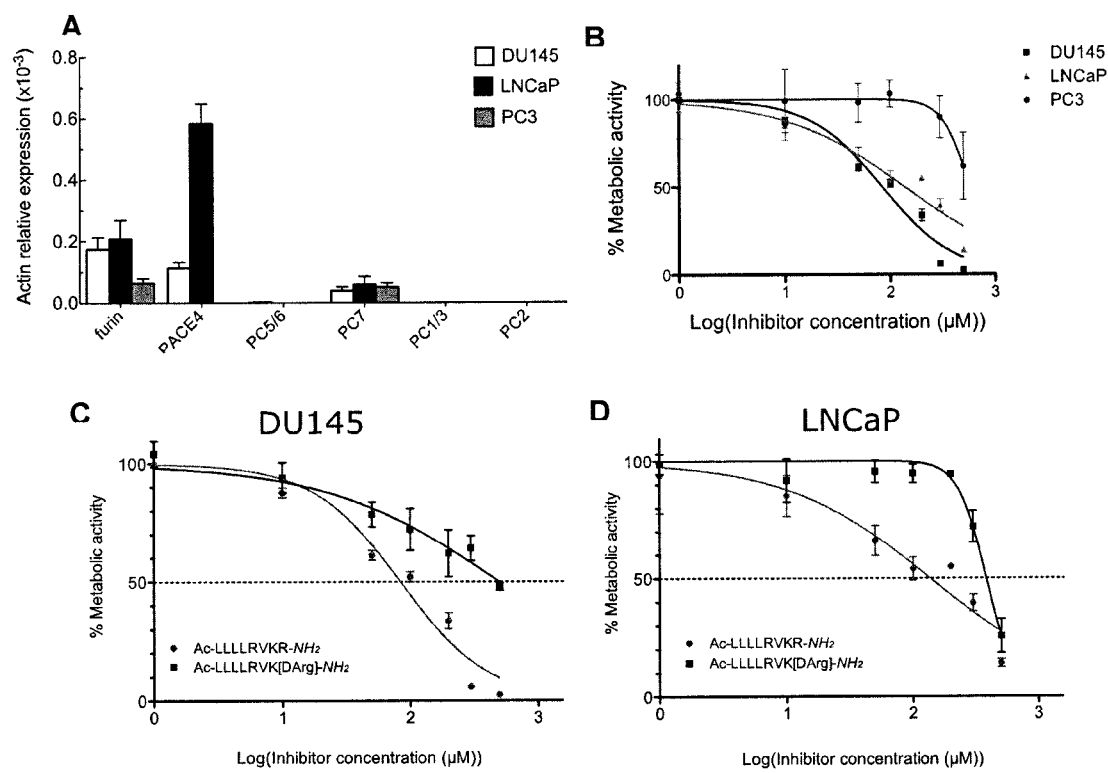
FIG. 1 illustrates the potential of the compounds described herein to act as an inhibitor of prostate cancer proliferation wherein in (A) PCs expression levels in DU145, LNCaP and PC3 prostate-cancer derived cell lines is shown; (B) MTT assays performed on those cell lines; and in (C) and (D) using MIT assay, it is observed that the peptide Ac-LLLLRVK[DArg]-NH$_2$ inhibits DU145 and LNCaP proliferation poorly as expected from inhibition constant values.

In a previous study, PACE4 was also proposed as a new therapeutic target in prostate cancer (D'Anjou et al., 2011, Transl Oncol., 4: 157-172). Using a molecular inhibition approach using the prostate cancer cell line DU145, derived from a human brain metastasis, it was demonstrated that the molecular inhibition of PACE4 in DU145 cells had dramatic effects on cell proliferation in vitro and in vivo. In the present disclosure, PACE4 expression levels in LNCaP and PC3 cell lines, additional prostate cancer cell lines, in comparison to DU145 cells, was measured using a RT-qPCR approach (FIG. 1A). PACE4 is most highly expressed in LNCaP cells, with nearly 6-fold higher levels than DU145 cells, but almost absent in PC3 cells. DU145 and LNCaP cells also exhibited higher levels of furin mRNA than PC3 cells. Similar expression levels are observed for PC5/6 and PC7 within all cell lines investigated and PC1/3 and PC2 are undetectable.

A series of PACE4 peptide inhibitors with varying degrees of selectivity and potency for PACE4 are known in the art. One particular compound stand out: LLLLRVKR-NH$_2$ (comprising four leucine and known as the "multi-Leu peptide" or "ML-peptide") (WO 2010/003231). The effects of the ML-peptide on cellular proliferation of DU145, LNCaP and PC3 cell lines using MTT assay is demonstrated herein (FIG. 1B). The ML-peptide showed a very poor inhibition of PC3 cells whereas the half maximal inhibitory concentrations (IC$_{50}$) were in the micromolar range for DU145 and LNCaP cells (103±29 and 180±57 µM, respectively). Thus, the ML-peptide inhibited the proliferation of DU145 and LNCaP cells, but not PC3 cells, showing a strong correlation with cellular PACE4 expression. A negative control ML-peptide was designed by substituting at the P1 position a DArg. As the P1 Arg position is critical for PC recognition, this modification strongly abrogates the observed effects, unless they are not PC-mediated. As expected, the peptide Ac-LLLLRVK-[DArg]-NH$_2$ showed a substantial loss of affinity in vitro going from a nM to a µM inhibitor (K$_i$'s=1380 and 2600 nM for PACE4 and furin, respectively). Consistent with this affinity loss, this peptide also showed a significant loss of potency in both DU145 (FIG. 1C) and LNCaP (FIG. 1D) cell-based assays (IC$_{50}$ 439±82 and 389±12 µM, respectively). The data demonstrates PACE4 inhibition decreases cell proliferation.

Increasing the affinity, potency, and/or stability of PACE4 inhibitors compared to the ML-peptide represented a promising avenue in developing effective compounds for cancer therapy in view of the results described hereinabove.

One of the keys to the development of potent and selective PC inhibitors is an understanding of the substrate-binding pocket. The deepest region of the substrate-binding pocket accommodates the consensus motif RXKR (P$_4$-P$_3$-P$_2$-P$_1$) nearly identical in all PCs. Potency and selectivity are determined by a less deeper region that interacts with P$_8$-P$_7$-P$_6$-P$_5$ of the inhibitor peptide (see Henrich et al., 2005, J. Mol. Biol., 345: 211-227; Fugere and Day, 2005, Trends Pharmacol. Sci., 26: 294-301; Henrich et al., 2003, Nat. Struct. Biol., 10: 520-526).

Endogenous inhibitors are often a good starting point in the development of pharmacological compounds. For example, proSAAS and the 7B2 C-terminal peptide are two endogenous inhibitors identified that inhibit PC1/3 and PC2, respectively. PC pro-domains are auto processed in cis by their cognate PC, but remain bound to the active site through their C-terminal PC-recognition sequence until the complex reaches the compartment of zymogene activation. Thus, pro-domains are dual-function molecules, being the first substrate and first inhibitor encountered by PCs in cells.

In order to potentially inhibit the effects of PACE4 in for example cancer proliferation, improved selective inhibitors were prepared and tested from the multi-Leu compound.

The nomenclature used to identify amino acid positions in the inhibitors disclosed herein is as follows:

```
Multi-Leu peptide or ML-petide
Ac-L-L-L-L-R-V-K-R-NH₂

Ac-P8-P7-P6-P5-P4-P3-P2-P1-NH₂
```

Figure 2:
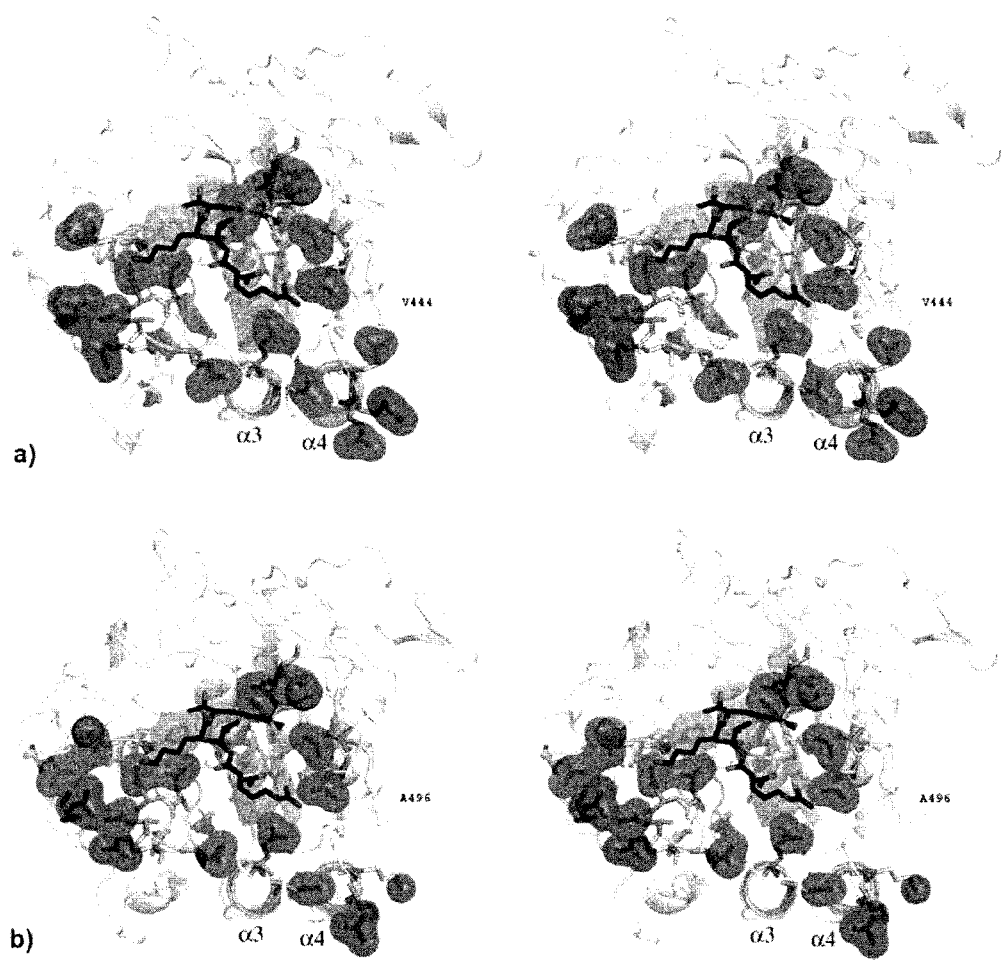
FIG. 2 illustrates homology analysis of the catalytic domain of PACE4 based on the crystal resolution of furin, where in (A) the catalytic site of furin is shown and in (B) the homologous PACE4 catalytic site is illustrated, showing the suicide inhibitor acetyl-RVKR-CMK (CMK-choloromethyl ketone) in the binding pocket.
Figure 3:
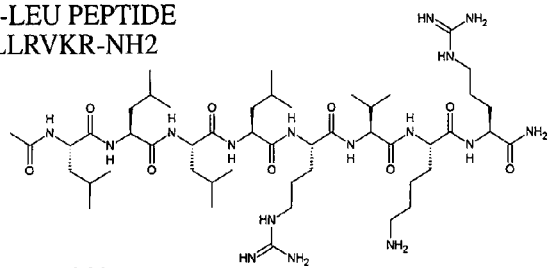
FIG. 3 illustrates peptidomimetic modifications used in the synthesis of multi-Leu variants and examples of variants.
Figure 3:
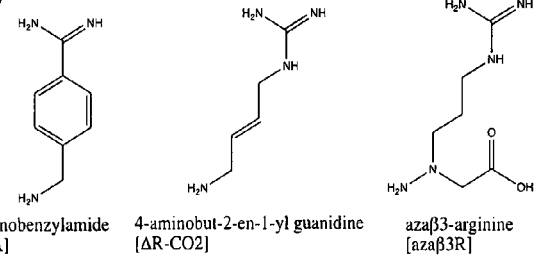
Figure 3:
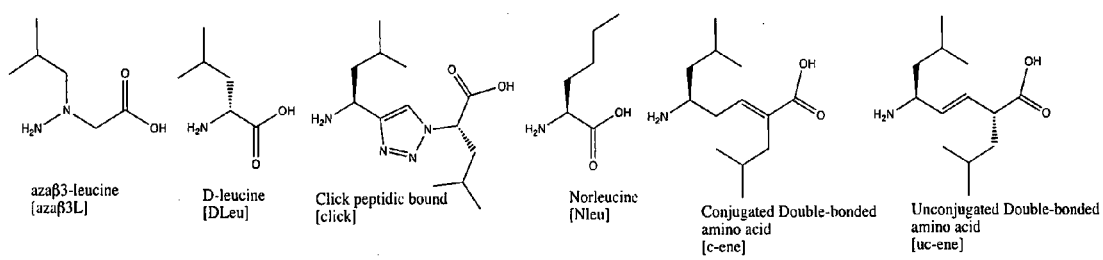
Figure 3:
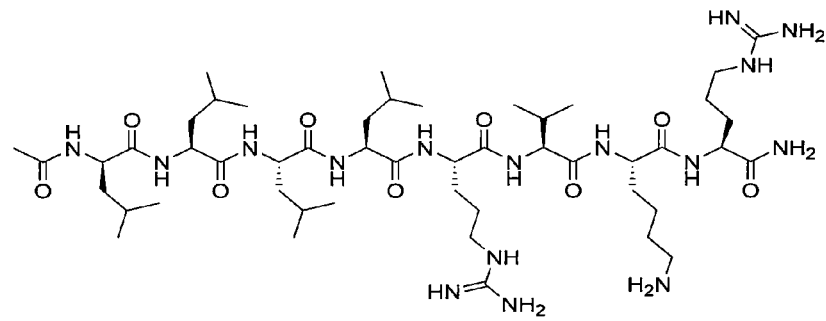
Figure 3:
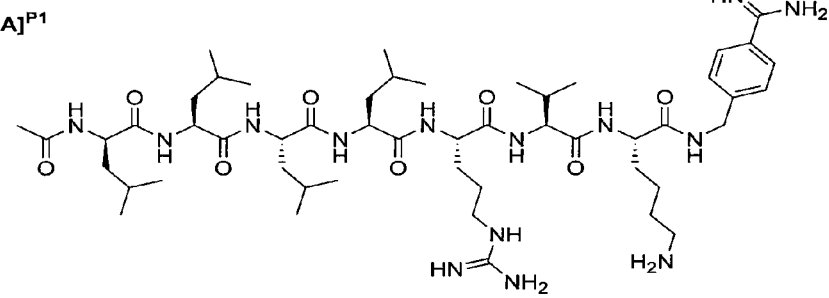

Firstly, based on homology analysis of the catalytic site of PACE4 with the furin crystal structure (FIG. 2), using the Modeller9v6 on Linux platform, structural modifications were made to the multi-Leu peptide in order to identify improved inhibitors. Multiples analogues of amino acids and pseudo peptide bounds were incorporated in the multi-Leu compound as illustrated in FIG. 3 in order to improve the stability and the potency of such compound.

Figure 4:
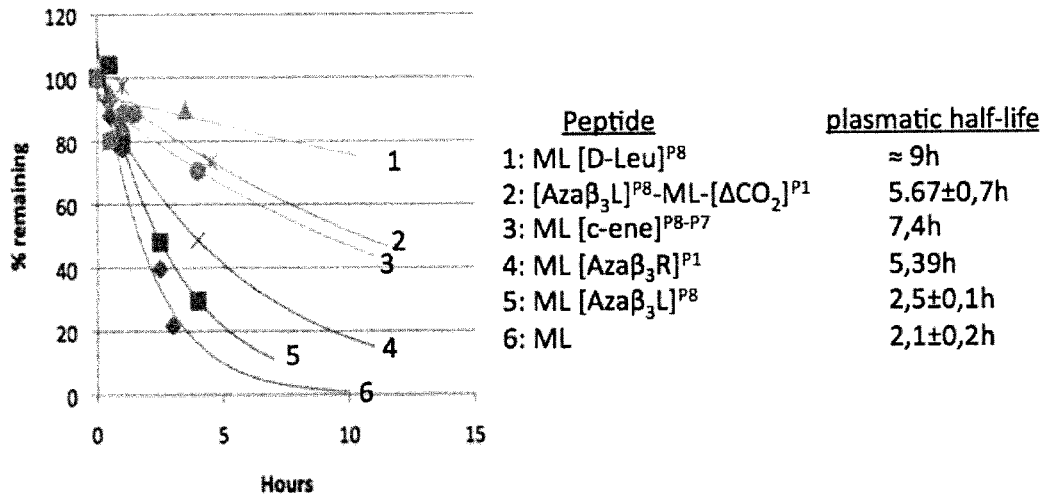
FIG. 4 illustrates plasmatic half-life curves measured for multi-Leu variants tested.

Multiple multi-Leu variants described in Table 1 were tested for their stability following incubation with DU145 cells, wherein their cellular stability and plasmatic half-life was measured. Examples of half-life curves are shown in FIG. 4.

TABLE 1

Multiple multi-Leu variants synthesized

| NAME | DESCRIPTION | K$_i$ for PACE4 | Stability (% remaining after 48 h) | Plasmatic half-life |
|---|---|---|---|---|
| Multi-Leu (ML) | Ac-LLLLRVKR-NH$_2$ | 38 nM | 56% | 2.1 ± 0.2 h |
| ML-[AMBA]$^{P1}$ | Ac-LLLLRVK-[AMBA] | 0.25 nM | ≈80% | N.A. |

TABLE 1-continued

Multiple multi-Leu variants synthesized

| NAME | DESCRIPTION | $K_i$ for PACE4 | Stability (% remaining after 48 h) | Plasmatic half-life |
|---|---|---|---|---|
| ML[Nle]$^{P5}$ | Ac-LLL[Nle]RVKR-$NH_2$ | 17 nM | 42% | N.A. |
| ML[Nleu]$^{P5-6-7-8}$ | Ac-[Nle][Nle][Nle][Nle]RVK-$NH_2$ | 344 nM | N.A. | N.A. |
| ML[Nle]$^{P8}$ | Ac[Nle]LLLRVKR-$NH_2$ | 37 nM | 67% | N.A. |
| ML[Nle]$^{P5-6-8}$ | Ac-[Nle][Nle]L[Nle]RVKR-$NH_2$ | 85 nM | 41% | N.A. |
| ML[click]$^{P8-P7}$ | Ac-L[click]LLLRVKR-$NH_2$ | 37 nM | 52% | 4.0 ± 0.5 h |
| ML[click]$^{P7-P6}$ | Ac-LL[click]LLRVKR-$NH_2$ | 600 nM | N.A. | 1.0 ± 0.2 h |
| ML[D-Leu]$^{P8}$ | Ac-[D-Leu]LLLRVKR-$NH_2$ | 52 nM | 48% | ≈9 h |
| ML[c-ene]$^{P8-P7}$ | Ac-L=LLLRVKR-$NH_2$ | 247 nM | N.A. | ≈7.4 ± 0.1 h |
| ML-[ΔR-$CO_2$]$^{P1}$ | Ac-LLLLRVK-[ΔR-COO] | 14 nM | 70% | N.A. |
| ML[Ser]-P5 | Ac-LLLSRVKR-$NH_2$ | 11 nM | 88% | 2.32 ± 0.04 h |
| [H2N-PEG8]-ML | Ac-[HN-PEG8]-LLLLRVKR-$NH_2$ | 23 nM | 64% | 1.3 ± 0.2 h |
| ML[Azaβ$_3$L]$^{P8}$ | Ac-[Azaβ$_3$L]LLLRVKR-$NH_2$ | 23 nM | 83% | 2.5 ± 0.1 h |
| [Azaβ$_3$L]$^{P8}$-ML-[ΔR-$CO_2$]$^{P1}$ | Ac-[Azaβ$_3$L]LLLRVKR-[ΔR-COO] | 2.1 nM | N.A. | 5.67 ± 0.07 h |
| ML[Azaβ$_3$L]$^{P7}$ | Ac-L[Azaβ$_3$L]LLLRVKR-$NH_2$ | 1243 nM | 72% | 3.38 ± 0.01 h |
| ML[Azaβ$_3$L]$^{P6}$ | Ac-LL[Azaβ$_3$L]LRVKR-$NH_2$ | 1535 nM | 84% | N.A. |
| ML[Azaβ$_3$L]$^{P5}$ | Ac-LLL[Azaβ$_3$L]RVKR-$NH_2$ | 619 nM | 71% | N.A. |
| ML[Azaβ$_3$R]$^{P1}$ | Ac-LLLLRVK[Azaβ$_3$R]-$NH_2$ | 460 nM | N.A. | 5.39 ± 0.08 |
| [D-Leu]$^{P8}$-ML | Ac-[D-Leu]-LLLRVKR-NH2 | 33 nM | N.A. | 6.3 h |
| [D-Leu]$^{P8}$-ML-[AMBA]$^{P1}$ | Ac-[D-Leu]-LLLRVK-[AMBA] | 8.8 nM | N.A. | 11.3 h |

Figure 5:
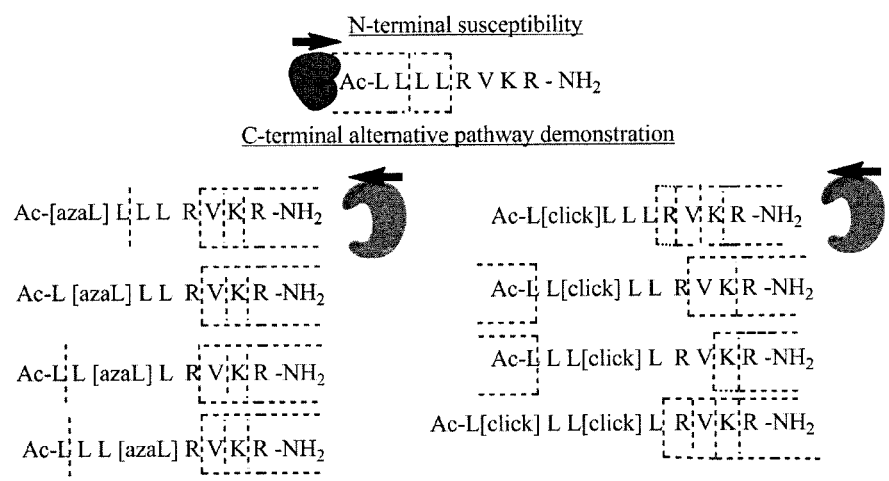
FIG. 5 illustrates the degradation kinetic of multi-Leu peptides showing that in absence of N-terminal protection, leucines are cleaved demonstrating a degradation by aminopeptidase.

Stabilisation strategy for multi-Leu variants was also assessed in presence of plasmatic protease. 8 variants protected at their N-terminal leucines were tested in order to establish their level of degradation since it is expected that N-terminal degradation will occur in absence of any modifications other than acetylation. Variants tested with azaβ$_3$-leucine at each individual position and "click" bonds between the different leucines of the N-terminal part of the variants were protected against degradation (see FIG. 3 for modifications). Results are shown in FIG. 5 demonstrating that degradation in presence of N-terminal protecting modifications occurs principally at the C-terminal part.

Degradation and stability assays results are not contradictory since N-terminal protection (conjugated double-bounded amino acid or "c-ene" link in P7-P8; D-leucine in P8; and azaβ$_3$-leucine in P8) increase the half-life of the variants versus the multi-Leu control (see Table 1).

Five inhibitors were identified has being the more potent and selective PAC4 inhibitors (Table 2):

TABLE 2

PACE4 inhibitors with improved potency and stability

| NAME | DESCRIPTION | $K_i$ for PACE4 | Stability (% remaining after 48 h) | Plasmatic half-life |
|---|---|---|---|---|
| Multi-Leu(ML) | Ac-LLLLRVKR-$NH_2$ | 38 nM | 56% | 2.1 ± 0.2 h |
| ML-[AMBA]$^{P1}$ | Ac-LLLLRVK-[AMBA] | 0.25 nM | ≈80% | N.A. |
| [Azaβ$_3$L]$^{P8}$-ML-[ΔR-$CO_2$]$^{P1}$ | Ac-[Azaβ$_3$L]LLLRVKR-[ΔR-COO] | 2.1 nM | N.A. | 5.67 ± 0.07 h |
| ML-[ΔR-$CO_2$]$^{P1}$ | Ac-LLLLRVK-[ΔR-COO] | 14 nM | 70% | N.A. |
| [D-Leu]$^{P8}$-ML | Ac-[D-Leu]-LLLRVKR-$NH_2$ | 33 nM | N.A. | 6.3 h |
| [D-Leu]$^{P8}$-ML-[AMBA]$^{P1}$ | Ac-[D-Leu]-LLLRVK[AMBA] | 8.8 nM | N.A. | 11.3 h |

Peptides Ac-LLLLRVK-[ΔR-COO] (or ML-[ΔR-CO$_2$]$^{P1}$), Ac-[Azaβ$_3$L]LLLRVK-[ΔR-COO] (or [azaβ$_3$L]$^{P8}$-ML-[ΔR-CO$_2$]$^{P1}$), Ac-LLLLRVK-[AMBA] (or ML-[AMBA]$^{P1}$) Ac[D-Leu]LLLRVKR-NH$_2$ (or [D-Leu]$^{P8}$-ML) Ac-[D-Leu]-LLLRVK-[AMBA] (or [D-Leu]$^{P8}$-ML-[AMBA]$^{P1}$)) have an increase half-life and potency for PACE4 and represent potent inhibitors of PACE4.

As seen in Table 3, the Ac-LLLLRVK-[ΔR-COO], Ac-[Azaβ$_3$L]LLLRVK-[ΔR-COO], Ac-LLLLRVK-[AMBA], Ac-[D-Leu]-LLLRVKR-NH$_2$, and Ac-[D-Leu]LLLRVK-[AMBA], peptides have a better selectivity for PACE4 than for furin. For example, Ac-LLLLRVK-[LR-COO] (11.4 time more selective), Ac-[Azaβ$_3$L]LLLRVK-[ΔR-COO] (3.8 time more selective) and Ac-LLLLRVK-[AMBA] (23.9 more selective) have a combined improved stability and potency for PACE4, still maintaining their specificity for PACE4.

TABLE 3

Structure-activity relationship of selected multi-Leu variants

| NAME | K$_i$ PACE4 (nM) | K$_i$ Furin (nM) | Selectivity index PACE4/furin |
|---|---|---|---|
| ML | 38 | 722 | 19 |
| ML-[AMBA]$^{P1}$ | 0.25 | 5.97 | 23.9 |
| [Azaβ$_3$L]$^{P8}$-ML-[ΔR—CO$_2$]$^{P1}$ | 2.11 | 7.90 | 3.8 |
| ML-[ΔR—CO$_2$]$^{P1}$ | 14 | 160 | 11.4 |
| [D-Leu]$^{P8}$-ML | 3 | 516 | ≈20 |
| [D-Leu]$^{P8}$-ML-[AMBA]$^{P1}$ | 8.8 | 13.0 | ≈1.5 |

Figure 6:
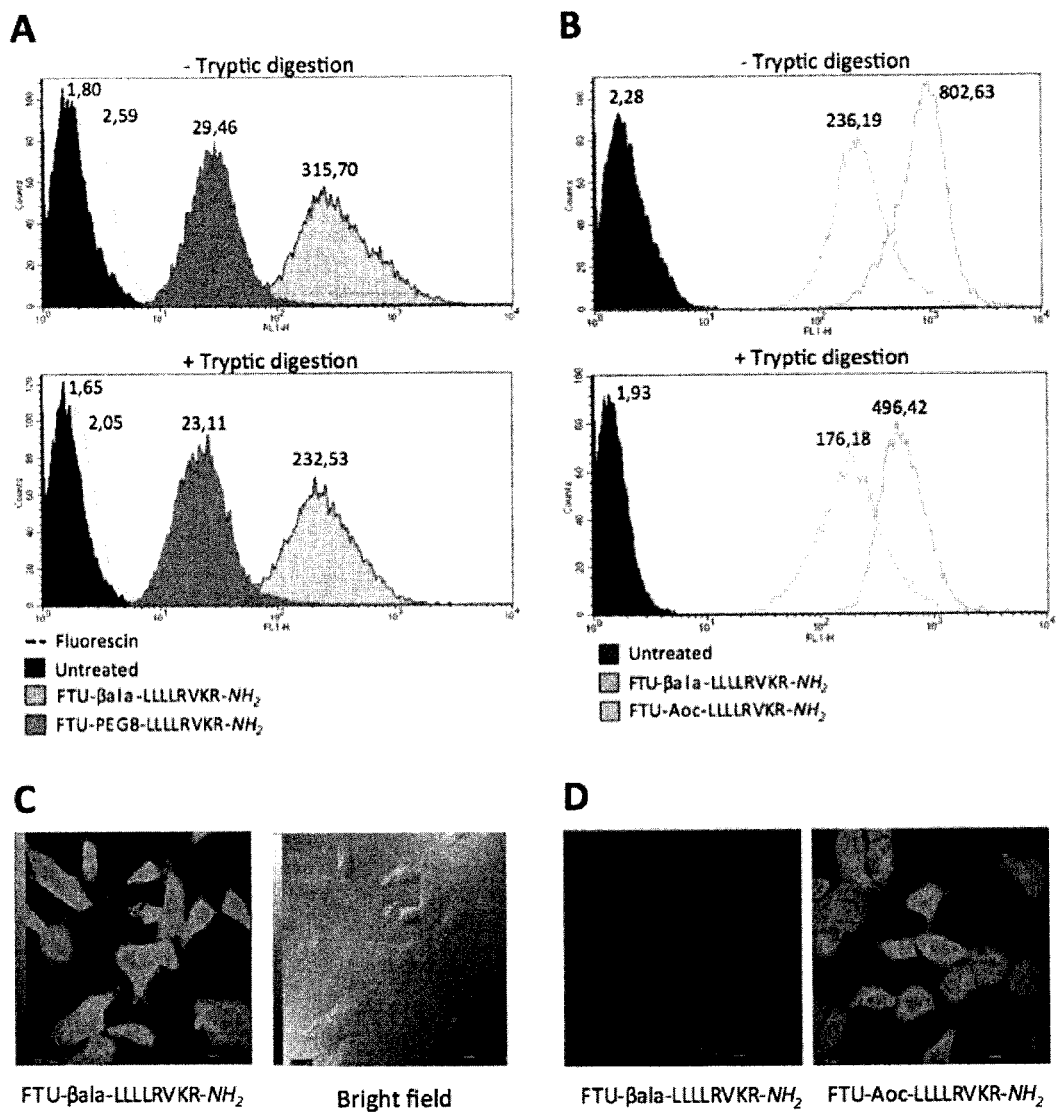
FIG. 6 illustrates the incorporation level of multi-Leu peptide in HT1080 cells, wherein in (A) the FTU-βAla-LLLLRVKR-NH$_2$ (FTU-fluorescein thiourea) and its variant FTU-PEG8-LLLLRVKR-NH$_2$ were tested; in (B) the incorporation of the FTU-βAla-LLLLRVKR-NH$_2$ and its variant FTU-Aoc-LLLLRVKR-NH$_2$ (Aoc-amino-octanoyl) were compared; and in (C) and (D) confocal microscopic images are shown of HT1080 cells treated with the FTU-βAla-LLLLRVKR-NH$_2$ and FTU-Aoc-LLLLRVKR-NH$_2$ peptides.

The addition of the lipid amino-octanoyl group increased the penetration of the multi-Leu molecule, reducing its IC$_{50}$ by 1.5 time (FIG. 6), translating in a 50% increase in its efficiency due to a gain of 50% internalisation, whereas the addition of de poly(8)-ethylene-glycol (PEGS) group decreases by 10 time the internalisation of the modified compound and increases its IC$_{50}$ by 5 time (see FIG. 6). Further modifying the inhibitors with the lipid amino-octanoyl group will increase their potency by increasing the penetration of the compound in targeted cell.

Consequently, the multi-Leu peptide was further modified by the addition of amino acid analogues and/or with pseudo peptide bounds which increase the protection of the modified peptides from peptidase and protease degradation. Gains in stability were also measured in vitro in tumoral prostatic human cells (DU145). Increase in stability of the variants was also measured in vivo (FIG. 4).

Figure 7:
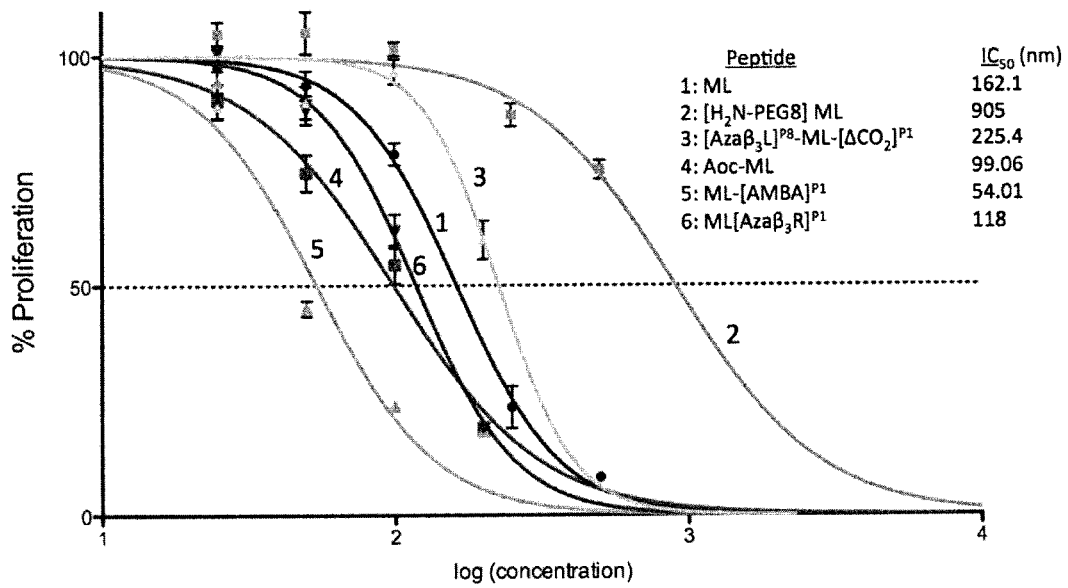
FIG. 7 illustrates the anti-proliferative activity of PACE4 inhibitors described herein.

With the objective to measure their anti-proliferative activity, multi-Leu variants were used in a proliferation assay measuring the mitochondrial metabolic activity (MTT) in DU145 cells. The ML-[AMBA], [Azaβ$_3$L]$^{P8}$-ML-[ΔR-CO$_2$]$^{P1}$ and ML-[ΔR-CO$_2$]$^{P1}$ all showed an increase of the anti-proliferative activity with an IC$_{50}$ lower than the IC$_{50}$ of the multi-Leu control (FIG. 7).

Anti-proliferative activity of the multi-leu variants was confirmed in LNCaP cells (Table 4).

TABLE 4

Proliferation assay measuring the mitochondrial metabolic activity (MTT) in DU145 cells and LNCaP cells

| Peptide | Description | IC$_{50}$ (μM) DU145 | IC$_{50}$ (μM) LNCaP |
|---|---|---|---|
| Multi-Leu (ML) | Ac-LLLLRVKR-NH$_2$ | 187 ± 44 | 180 ± 57 |
| [D-Leu]$^{P8}$-ML | Ac-[D-Leu]-LLLRVKR-NH$_2$ | 66 ± 26 | 181 ± 59 |
| [D-Leu]$^{P8}$-ML-[AMBA]$^{P1}$ | Ac-[D-Leu]-LLLRVK-[AMBA] | 43 ± 15 | 86 ± 18 |
| [PEG$_8$]-[D-Leu]$^{P8}$-ML-[AMBA]$^{P1}$ | Ac-[PEG$_8$]-[D-Leu]-LLLRVK-[AMBA] | 88 ± 49 | >300 |

Figure 8:
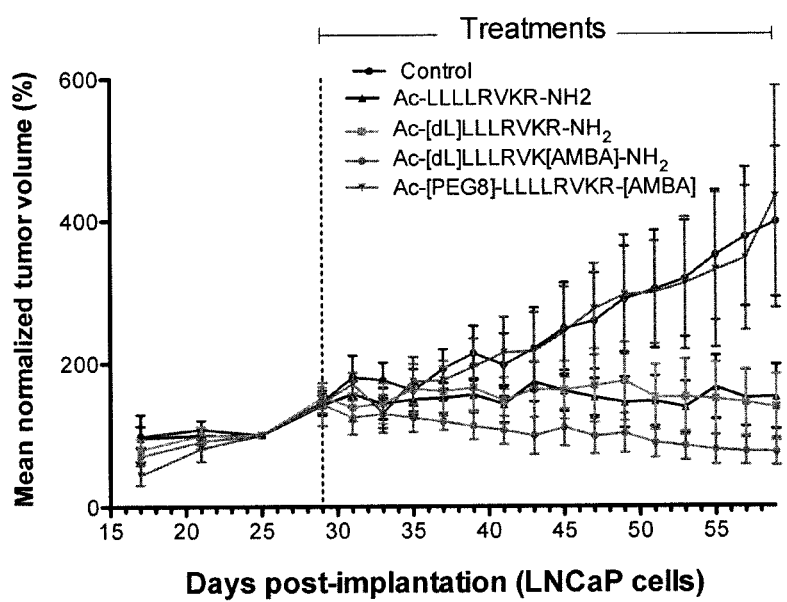
FIG. 8 is a histogram showing tumor regression in vivo observed with treatment with ML-variants.

The ML-peptide and three variants were administered intratumorally (50 μg/48 h) to immunosuppressed mice growing LNCaP tumors. Treatment with all tested compounds, with the exception of [PEG$_8$]-[D-Leu]$^{P8}$-ML-[AMBA]$^{P1}$, showed a decrease in tumor volume (see FIG. 8), the [D-Leu]$^{P8}$-ML-[AMBA]$^{P1}$ being consistently the more potent compound in this in vivo test.

Figure 9:
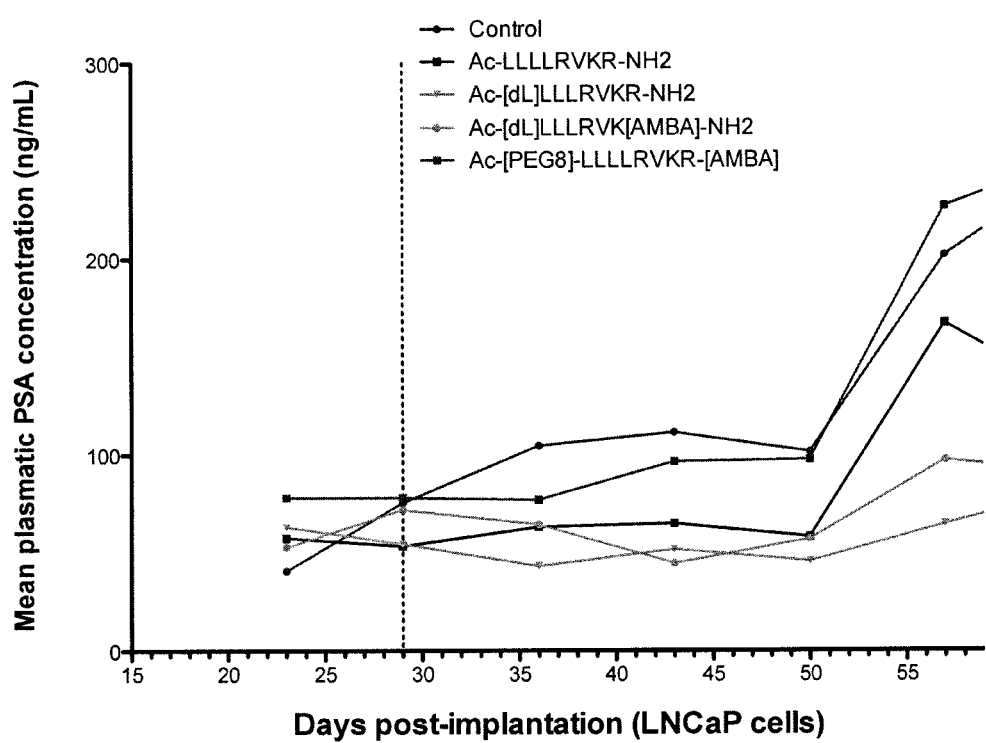
FIG. 9 is a histogram analysis of prostate-specific antigen (PAS) level in treated tumors with ML-peptide and ML variants.

Effect on the secreted concentration of the prostate-specific antigen (PSA) was also measured. As seen in FIG. 9, plasmatic concentration of PSA decreased with treatment with [D-Leu]$^{P8}$-ML-[AMBA]$^{P1}$ and [D-Leu]$^{P8}$-ML.

Figure 10:
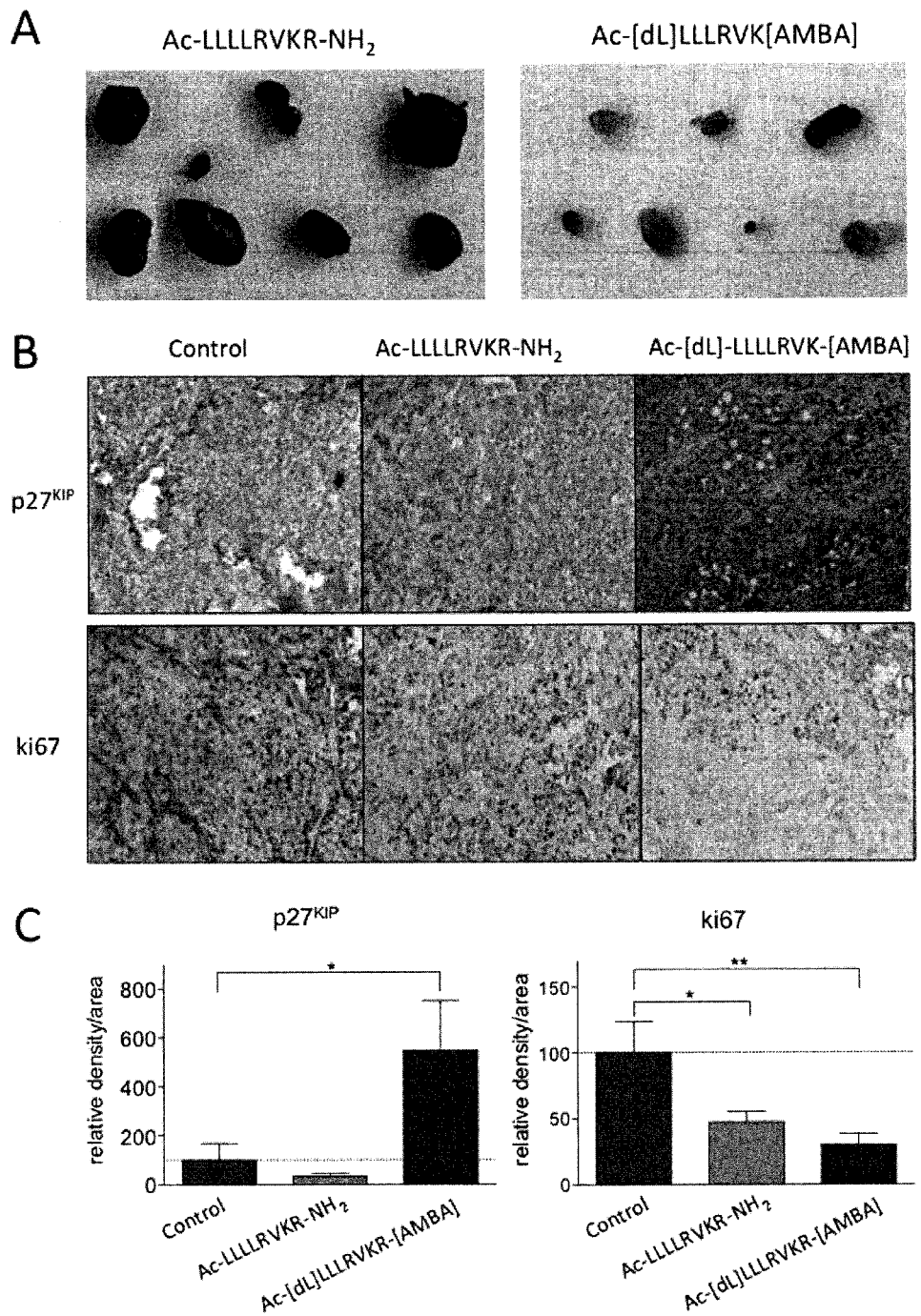
FIG. 10 illustrates effects observed on tumors treated with the ML-peptide and with the [D-Leu]$^{P8}$-ML-[AMBA]$^{P1}$ variant, wherein in (A) a photographic representation of treated tumors is shown; and in (B) and (C) a immunocytochemistry analysis of the level of p27$^{KIP}$ and ki67 markers is measured.

Once the LNCaP tumors were treated with the ML-peptide or with the [D-Leu]$^{P8}$-ML-[AMBA]$^{P1}$ variant, the tumors were excised. As seen in FIG. 10A, tumors treated with the [D-Leu]$^{P8}$-ML-[AMBA]$^{P1}$ variant are smaller and have a white appearance, reflecting a decrease in blood flow to the treated tumors.

Levels of p27KIP, a marker used to study cell cycle, and of ki67, cellular marker for proliferation, were measured by immunocytochemistry in excised tumors. As seen in FIGS. 10B and 10C, treatment of tumors with [D-Leu]$^{P8}$-ML-[AMBA]$^{P1}$ increased the level of p27KIP and decreased the level of Ki67 compared to levels seen with ML-peptide treated tumors and in untreated tumors. p27$^{KIP}$ is a cyclin dependent kinase (CDK) inhibitor protein, that binds and prevents the activation of cyclin E-CDK2 or cyclin D-CDK4 complexes, and thus controls the cell cycle progression at the G1 phase. Ki67 is a nuclear protein associated with ribosomal RNA transcription and is a cellular marker that is strictly associated with cell proliferation. Thus, treated cancer cells are induced into quiencence and reduced proliferation.

Figure 11:
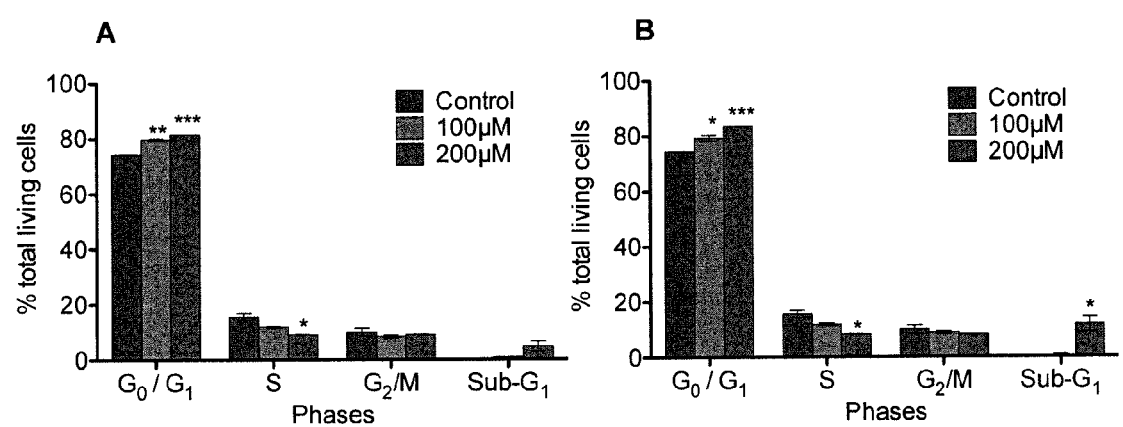
FIG. 11 illustrates the cell cycle analysis data of traited LNCapcells with (A) Ac-LLLLRVKR-NH$_2$ and (B) Ac-[D-Leu]-LLLLRVKR-NH$_2$.

In order to obtain further support for the antiproliferation effects observed, a DNA content analysis was performed on LNCaP treated cells with 100 μM or 200 μM of ML-peptide and the modified analog Ac-[D-Leu]LLLLRVKR-NH$_2$ (FIG. 11). A dose-dependant G$_0$/G$_1$ accumulation and S phase decrease is observed following exposure to ML-peptide and the modified analog Ac-[D-Leu]LLLLRVKR-NH$_2$ (Table 5). Following a 200 μM treatment with the Ac-[D-Leu]LLL-RVKR-NH$_2$, a 10% increase in the G$_0$/G$_1$ population was observed along with an increased in cells with hypodiploid DNA content (sub-G$_1$) proportions, which represent apoptotic cells.

TABLE 5

Cell cycle analysis of ML- and variant-treated LNCaP

| Phase | Control | Ac-LLLLRVKR—NH$_2$ | | Ac-[dL]LLLRVKR—NH$_2$ | |
|---|---|---|---|---|---|
| | | 100 μM | 200 μM | 100 μM | 200 μM |
| G0/G1 | 74.3 ± 0.1 | 79.7 ± 0.4 | 81.5 ± 0.0 | 79.3 ± 1.0 | 83.4 ± 0.0 |
| S | 15.6 ± 1.3 | 11.9 ± 0.2 | 9.3 ± 0.1 | 11.8 ± 0.5 | 8.4 ± 0.1 |
| G2/M | 10.1 ± 1.4 | 8.4 ± 0.6 | 9.2 ± 0.1 | 8.9 ± 0.5 | 8.3 ± 0.1 |
| Sub-G1 | 0.3 ± 0.2 | 1.0 ± 0.0 | 4.8 ± 1.7 | 0.4 ± 0.6 | 11.8 ± 2.7 |

A dose-dependent accumulation of cells in $G_0/G_1$ phase is noted, thus preventing cells entry into S phase. The transition between $G_1$ and S phase is a finely regulated mechanism controlled by a combination of environmental considerations mostly influenced by the presence of growth signals and the discontinuation of extracellular inhibitory signals. The observation of apoptosis following an exposure to 200 μM Ac-[D-Leu]-LLLRVKR-NH$_2$ in LNCaP cells is explained by the fact that cell cycle arrest is usually poorly tolerated and prolonged cytostasis must be escaped by death. This results confirms that the more potent and stable versions of the ML-peptide inhibitor as described herein result in improved drugs that reduce prostate cancer cell proliferation as well as inducing specific cell death.

It is encompassed herein a composition comprising the PACE4 inhibitors described herein and a carrier.

In accordance with the present description, a carrier or "pharmaceutical carrier" is a pharmaceutically acceptable solvent, suspending agent or any other pharmacologically inert vehicle for delivering one or more active compounds to an animal, and is typically liquid or solid. A pharmaceutical carrier is generally selected to provide for the desired bulk, consistency, etc., when combined with components of a given pharmaceutical composition, in view of the intended administration mode. Typical pharmaceutical carriers include, but are not limited to binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycotate, etc.); and wetting agents (e.g., sodium lauryl sulphate, etc.).

In another embodiment, the composition further comprises at least one anti-cancer drug. "Concurrent administration" and "concurrently administering" as used herein includes administering a composition as described herein and an anti-cancer drug, in admixture, such as, for example, in a pharmaceutical composition, or as separate formulation, such as, for example, separate pharmaceutical compositions administered consecutively, simultaneously, or at different times.

The composition can be adapted for delivery by at least one of the following route selected from the group consisting of oral, mucosal, intranasal, intraocular, intratracheal, intrabronchial, intrapleural, intraperitoneal, intracranial, intramuscular, intravenous, intraarterial, intralymphatic, subcutaneous, intratumoral, gastric, enteral, colonic, rectal, urethral and intravesical route.

There is provided a method of reducing the proliferation of a cell in a subject or reducing tumor growth, comprising administering the PACE4 inhibitors or the composition as defined herein to the subject, thereby reducing the proliferation of the cell in the subject.

Thus, it is provided a method for the treatment of a cancer in a subject, comprising administering to said subject a therapeutically effective amount of the PACE4 inhibitors or the composition as defined herein, thereby treating cancer in the subject.

Preferably, the cell is in a subject. More preferably, the cell is a cancer cell. More preferably, the cell has increased PACE4 activity.

There is also provided the use of the PACE4 inhibitors or the composition as defined herein in the manufacture of a medicament for treating cancer in a subject.

More specifically, the cancer is a prostate cancer or a metastasis thereof.

The cancer encompassed herein is breast cancer, glioma, large intestinal cancer, lung cancer, small cell lung cancer, stomach cancer, liver cancer, blood cancer, bone cancer, pancreatic cancer, skin cancer, head or neck cancer, cutaneous or intraocular melanoma, uterine sarcoma, ovarian cancer, rectal or colorectal cancer, anal cancer, colon cancer, fallopian tube carcinoma, endometrial carcinoma, cervical cancer, vulval cancer, squamous cell carcinoma, vaginal carcinoma, Hodgkin's disease, non-Hodgkin's lymphoma, esophageal cancer, small intestine cancer, endocrine cancer, thyroid cancer, parathyroid cancer, adrenal cancer, soft tissue tumor, urethral cancer, penile cancer, prostate cancer, chronic or acute leukemia, lymphocytic lymphoma, bladder cancer, kidney cancer, ureter cancer, renal cell carcinoma, renal pelvic carcinoma, CNS tumor, glioma, astrocytoma, glioblastoma multiforme, primary CNS lymphoma, bone marrow tumor, brain stem nerve gliomas, pituitary adenoma, uveal melanoma, testicular cancer, oral cancer, pharyngeal cancer, pediatric neoplasms, leukemia, neuroblastoma, retinoblastoma, glioma, rhabdomyoblastoma or sarcoma.

The composition can be formulated for concurrent administration during a suitable anti-cancer therapy, such as a surgical procedure, chemotherapy, hormonal therapy and localization radiation.

The composition described herein can be used either alone or in combination with other anti-cancer compound such as Acivicin; Aclarubicin; Acodazole Hydrochloride; Acronine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Fluorocitabine; Fosquidone; Fostriecin Sodium; Gemcitabine; Gemcitabine Hydrochloride; Hydroxyurea; Idarubicin Hydrochloride;

Ifosfamide; Ilmofosine; Interferon α-2a; Interferon α-2b; Interferon α-n1; Interferon α-n3; Interferon β-1a; Interferon γ-1b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrim. Streptozocin; Sulofenur; Talisomycin; Taxol; Taxotere; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; or Zorubicin Hydrochloride.

Other anti-cancer drugs include: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexifosfamide; dexrazoxane; dexverapamil; diaziquone; didemnin B; didox; diethylnorspermine; dihydro-5-azacytidine; dihydrotaxol, 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunornicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-irinotecan; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anti cancer compound; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide. modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene dichloride; topotecan; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Anti-cancer supplementary potentiating compounds include: Tricyclic anti-depressant drugs (e.g., imipramine, desipramine, amitryptyline, clomipramine, trimipramine, doxepin, nortriptyline, protriptyline, amoxapine and maprotiline); non-tricyclic anti-depressant drugs (e.g., sertraline, trazodone and citalopram); Ca++ antagonists (e.g., verapamil, nifedipine, nitrendipine and caroverine); Calmodulin inhibitors (e.g., prenylamine, trifluoroperazine and clomipramine); Amphotericin B; Triparanol analogues (e.g., tamoxifen); antiarrhythmic drugs (e.g., quinidine); antihypertensive drugs (e.g., reserpine); Thiol depleters (e.g., buthionine and sulfoximine) and multiple drug resistance reducing compounds such as Cremaphor EL.

Other compounds which are useful in combination therapy include the antiproliferation compound, Piritrexim Isethionate; the antiprostatic hypertrophy compound, Sitogluside; the benign prostatic hyperplasia therapy compound, Tamsulosin Hydrochloride; the prostate growth inhibitor, Pentomone; radioactive compounds such as Fibrinogen I 125, Fludeoxyglucose F 18, Fluorodopa F 18, Insulin I 125, Insulin I 131, Iobenguane I 123, Iodipamide Sodium I 131, Iodoantipyrine I 131, Iodocholesterol I 131, Iodohippurate Sodium I 123, Iodohippurate Sodium I 125, Iodohippurate Sodium I 131, Iodopyracet I 125, Iodopyracet I 131, Iofetamine Hydrochloride I 123, Iomethin I 125, Iomethin I 131, Iothalamate Sodium I 125, Iothalamate Sodium I 131, Iotyrosine I 131, Liothyronine I 125, Liothyronine I 131, Merisoprol Acetate Hg 197, Merisoprol Acetate Hg 203, Merisoprol Hg 197, Selenomethionine Se 75, Technetium Tc 99m Antimony Trisulfide Colloid, Technetium Tc 99m Bicisate, Technetium Tc 99m Disofenin, Technetium Tc 99m Etidronate, Technetium Tc 99m Exametazime, Technetium Tc 99m Furifosmin, Technetium Tc 99m Gluceptate, Technetium Tc 99m Lidofenin, Technetium Tc 99m Mebrofenin, Technetium Tc 99m Medronate, Technetium Tc 99m Medronate Disodium, Technetium Tc 99m Mertiatide, Technetium Tc 99m Oxidronate, Technetium Tc 99m Pentetate, Technetium Tc 99m Pentetate Calcium Trisodium, Technetium Tc 99m Sestamibi, Technetium Tc 99m Siboroxime, Technetium Tc 99m Succimer, Technetium Tc 99m Sulfur Colloid, Technetium Tc 99m Teboroxime, Technetium Tc 99m Tetrofosmin, Technetium Tc 99m Tiatide, Thyroxine I 125, Thyroxine I 131, Tolpovidone I 131, Triolein I 125 and Triolein I 131.

The PACE4 inhibitors or the composition as defined herein lower or inhibit PACE4 activity in a cell, reducing proliferation of a cell in a subject, and for reducing tumor growth in a subject.

The present disclosure will be more readily understood by referring to the following examples which are given to illustrate embodiments rather than to limit its scope.

EXAMPLE I

Preparation of the PACE4 Inhibitors

The compounds of the present disclosure can be prepared according to the procedures denoted in the following reaction Schemes and Examples or modifications thereof using readily available starting materials, reagents, and conventional procedures or variations thereof well-known to a practitioner of ordinary skill in the art of synthetic organic chemistry. Specific definitions of variables in the Schemes are given for illustrative purposes only and are not intended to limit the procedures described.

Scheme 1: General synthesis of Synthesis of Fmoc-α-methyl-L-Arg(Boc)2-OH.

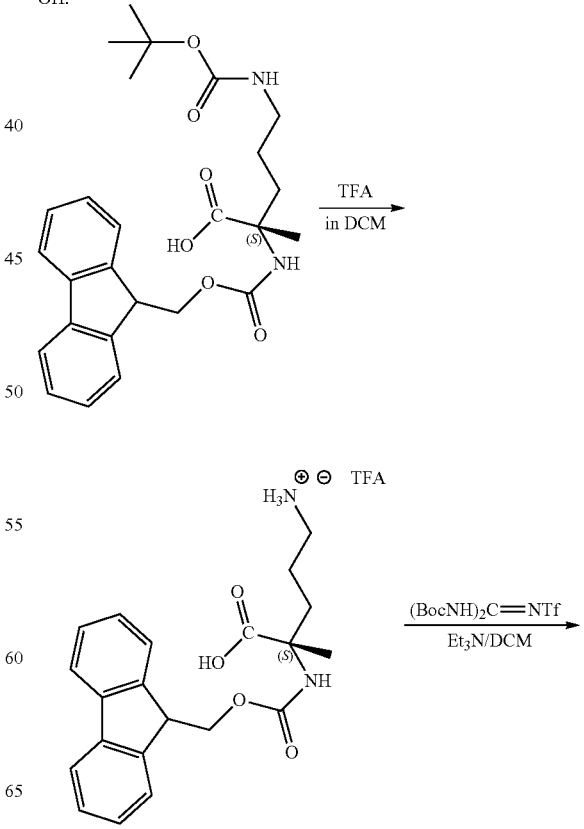

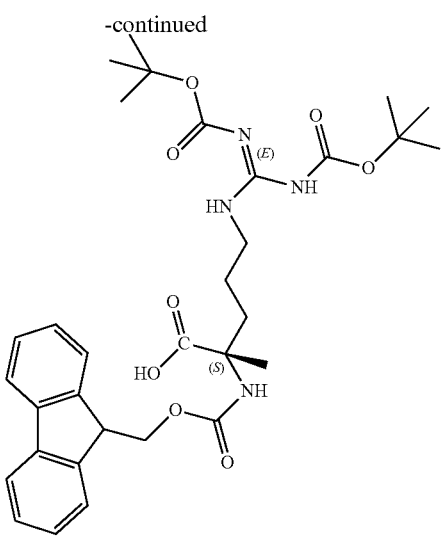

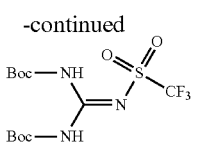

(BocNH)₂C=NTf stands for:

The synthesis of Fmoc-α-methyl-L-Arg(Boc)₂-OH was performed by guanidinylation of commercially available Fmoc-α-methyl-L-Orn-OH.

The synthesised Fmoc-α-methyl-L-Arg(Boc)₂-OH was used in peptide synthesis to generate an α-methyl-L-Arg peptide analogues. As illustrated in scheme 2, the 2-chlorotrityl resin is used for synthesis of protected peptide for further amidation on C-terminus with AMBA or other amines.

Scheme 2: General synthesis of protected peptide with the 2-chlorotrityl resin.

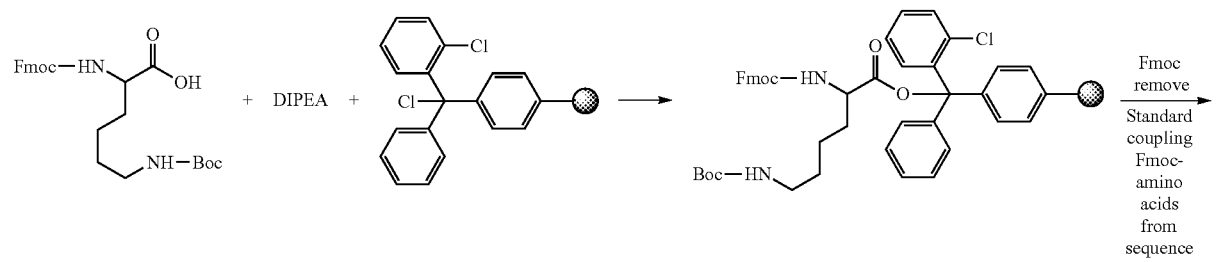

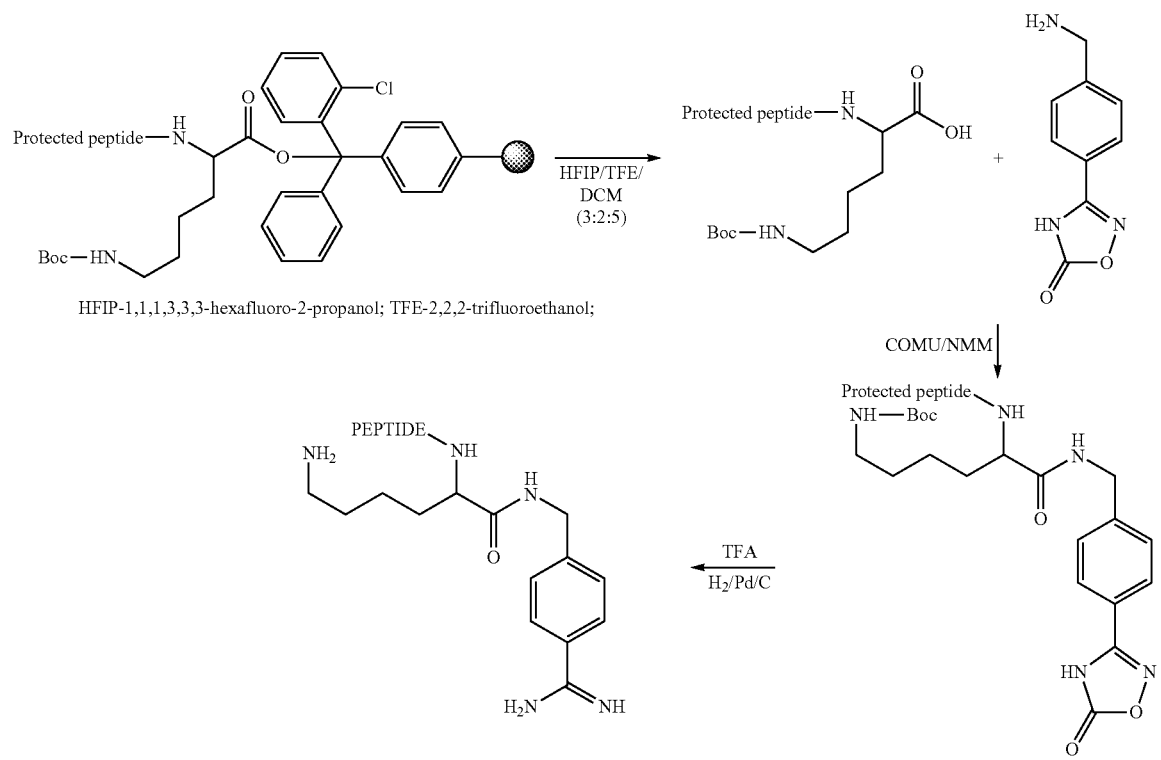

HFIP-1,1,1,3,3,3-hexafluoro-2-propanol; TFE-2,2,2-trifluoroethanol;

As illustrated in scheme 3, the hydrazine resin is used for the solid phase synthesis of protected peptide, where amidation of peptide occurs on C-terminus.
Scheme 3: General synthesis of protected peptide with the hydrazine resin.
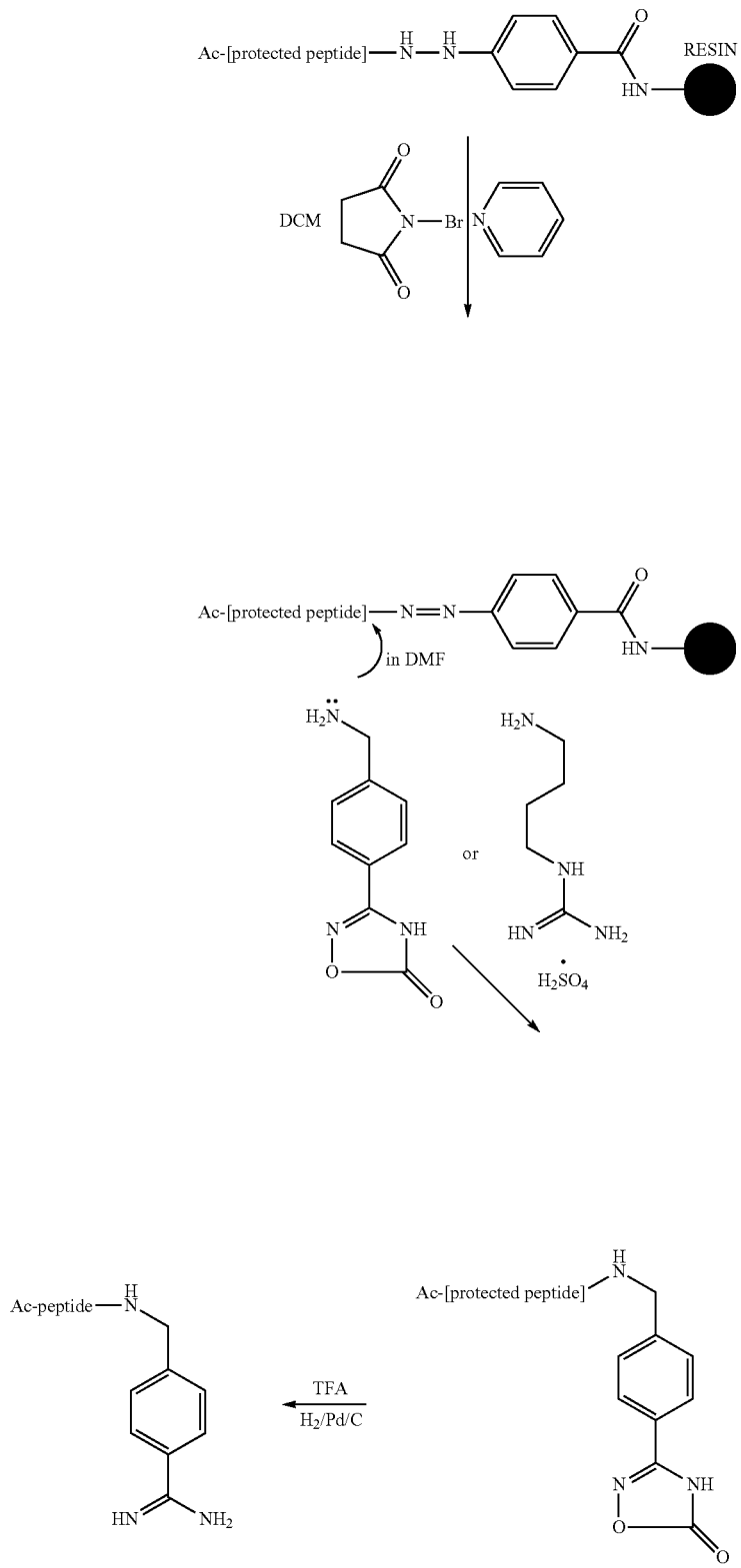

Scheme 4: General synthesis of 4-amidinobenzylamine (AMBA).

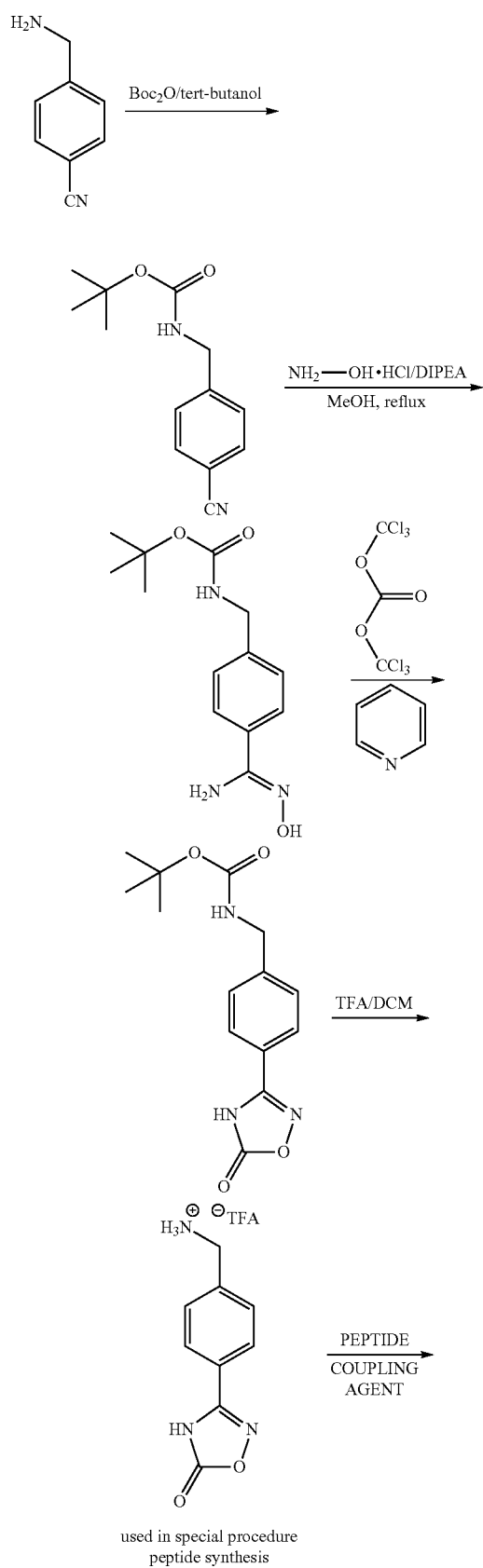

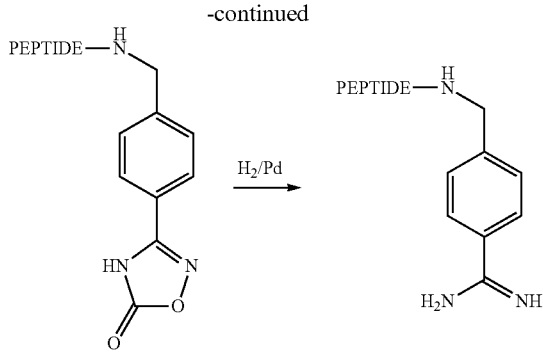

DIPEA = diisopropylethylamine; DCM = dichloromethane; TFA = trifluro acetic acid; Boc₂O = di-tert-butyl dicarbonate.

Scheme 5: General synthesis of inactive "Hector" (Phe derivative) analogue.

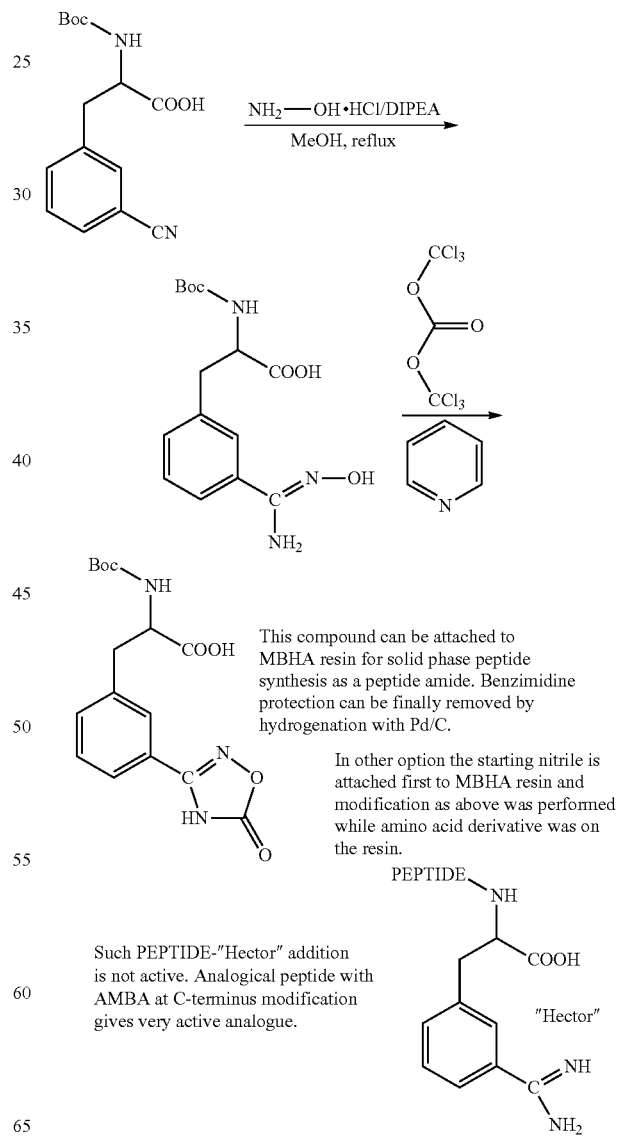

This compound can be attached to MBHA resin for solid phase peptide synthesis as a peptide amide. Benzimidine protection can be finally removed by hydrogenation with Pd/C.

In other option the starting nitrile is attached first to MBHA resin and modification as above was performed while amino acid derivative was on the resin.

Such PEPTIDE-"Hector" addition is not active. Analogical peptide with AMBA at C-terminus modification gives very active analogue.

Scheme 6: General synthesis of aza-β3-arginine amino acid.
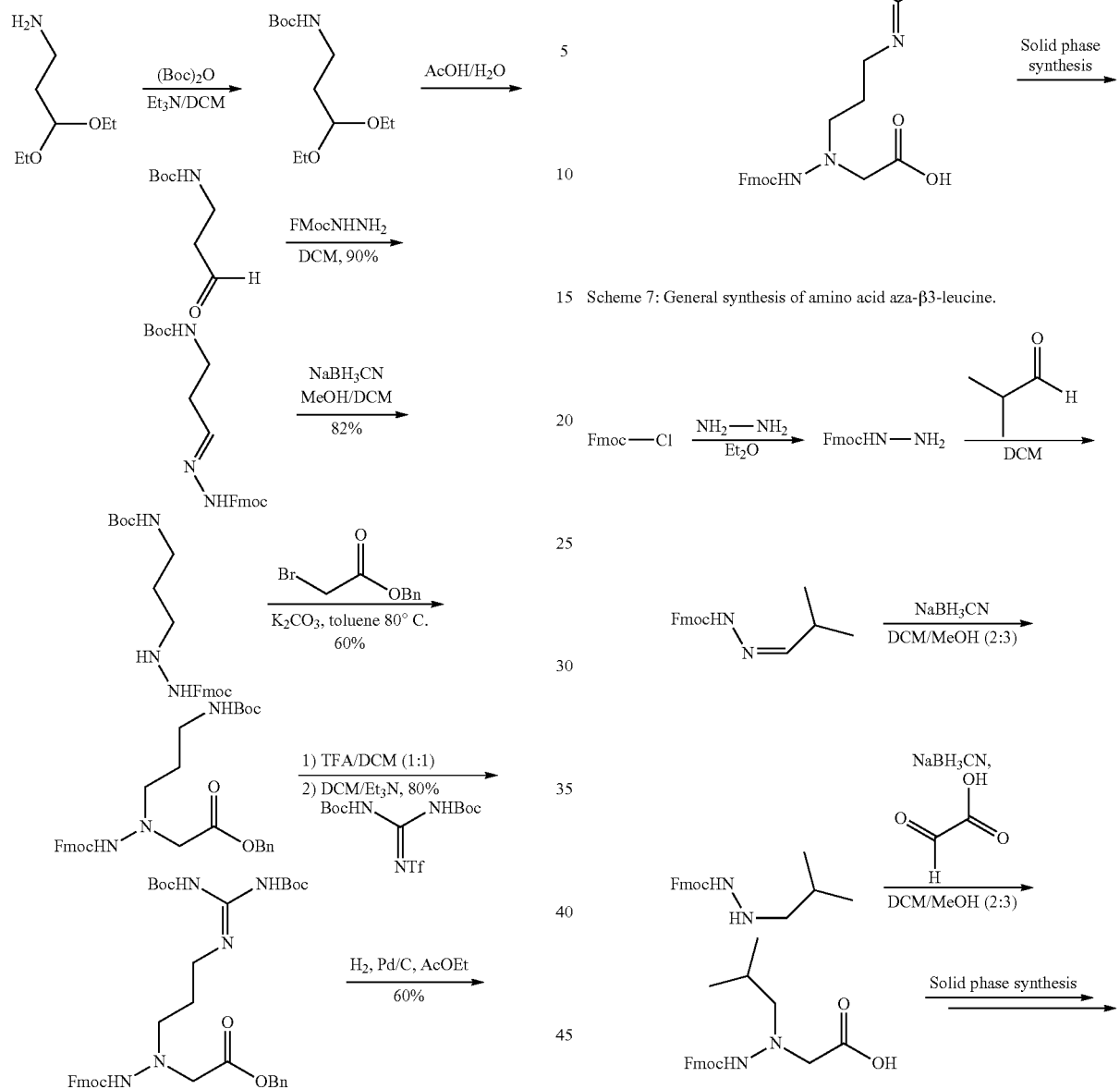
Scheme 7: General synthesis of amino acid aza-β3-leucine.
Scheme 8: General synthesis of 4-aminobut-2-en-1-yl guanidine.
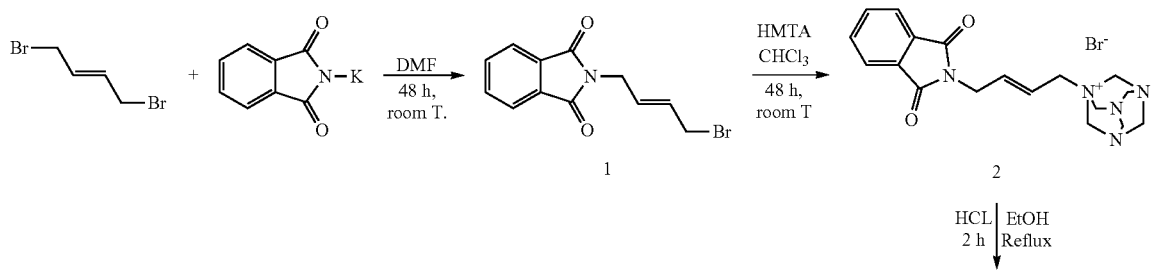

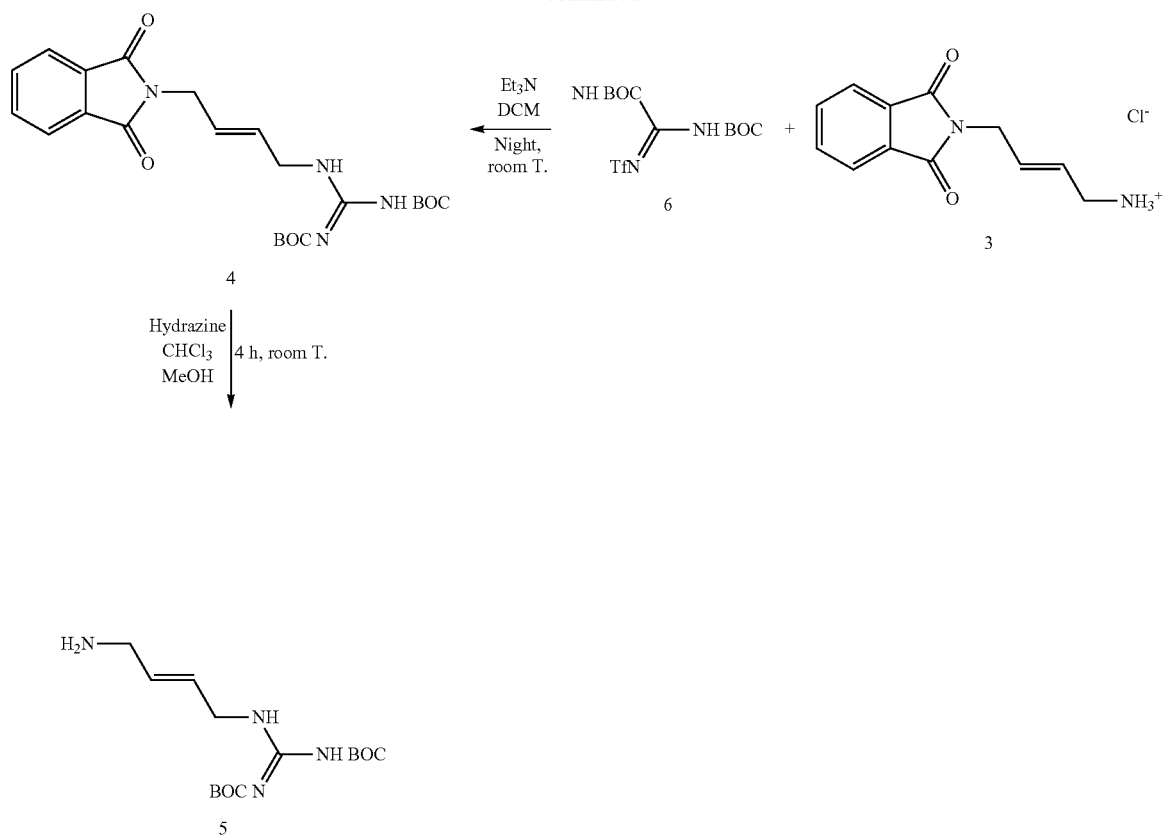
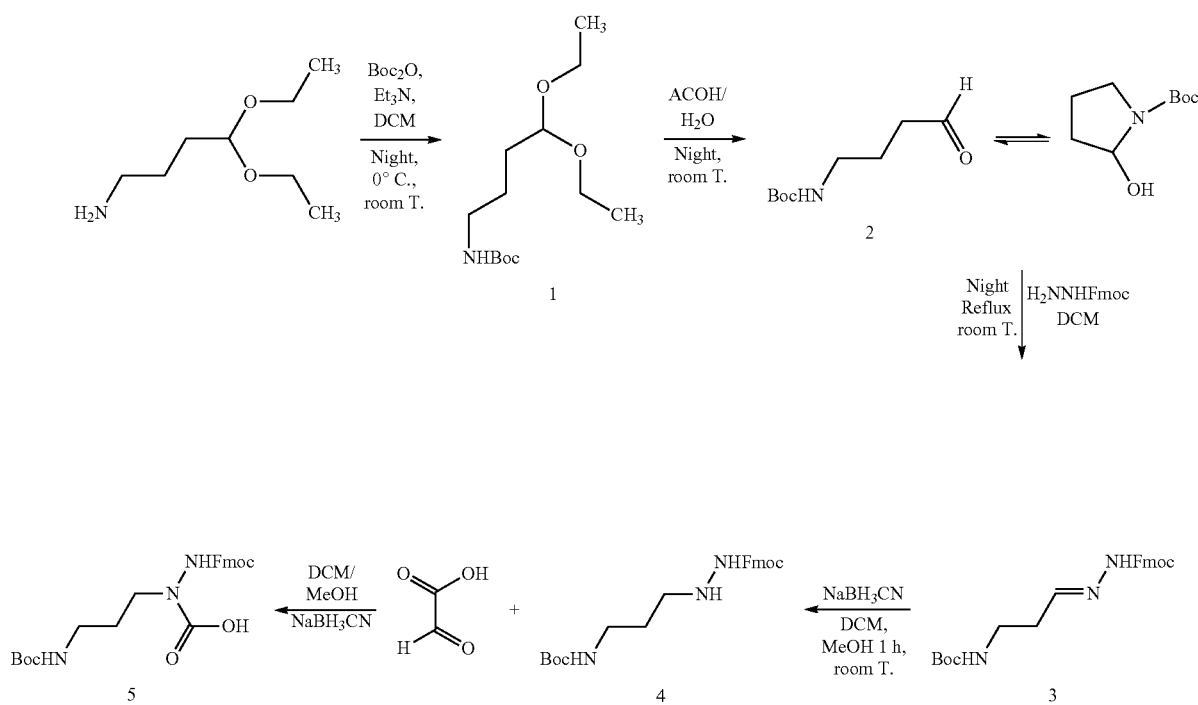
Scheme 9: General synthesis of aza-β3-lysine amino acid.

The following examples are given only to illustrate the invention and should not be regarded as constituting any limitation of the scope of the invention in its broadest meaning.

EXAMPLE 1

Synthesis of Aza-β3-arginine Amino Acid

Step 1: Protection of the Amine

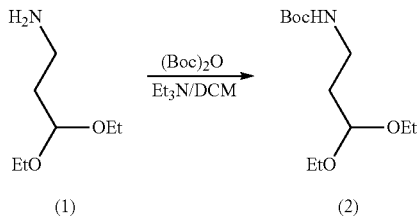 [SMILES: "(Boc)2O" ; CCOC(CCN)OCC ; CCOC(CCNC(=O)OC(C)(C)C)OCC]

3,3-diethoxypropan-1-amine (1) (5.24 g, 35.6 mmol) was diluted in a mixture of dichloromethane (80 mL) and triethylamine (5.12 mL). The solution was cooled to 0° C., and a solution of di-tert-butyl-dicarbonate (7.85 g, 35.97 mmol) in dichloromethane (20 mL) was slowly added over a 15-minute period. The mixture was stirred for 16 h, at room temperature. The organic phase was washed with 1N HCl (1×100 mL), 0.5N HCl (1×100 mL), and brine (2×100 mL) before it was dried with anhydrous magnesium sulphate, filtered and concentrated. Le crude product was purified by flash chromatography on silica gel (eluent:hexanes/ethyl acetate 7:3). The protected amine was obtained as a yellow oil (8.36 g, 94%). $^1$H NMR (300 MHz, CDCl$_3$) δ (ppm) 4.93 (s, 1H), 4.53 (t, 1H, J=5.5 Hz), 3.56 (d-quint, 4H, J=38.9 Hz, J=2.3 Hz), 3.20 (q, 2H, J=6.2 Hz), 1.79 (q, 2H, J=6.2 Hz), 1.42 (s, 9H), 1.19 (t, 6H, J=7.1 Hz). $^{13}$C NMR (75.5 MHz, CDCl$_3$) δ (ppm) 155.9, 101.9, 78.9. 61.5, 36.7, 33.4, 28.4, 15.3. IR (CHCl$_3$) ν (cm$^{-1}$) 3363 (br), 2979, 2920, 2880, 1708, 1514, 1448, 1393, 1365, 1171, 1139, 1065.

Step 2: Preparation of the Aldehyde

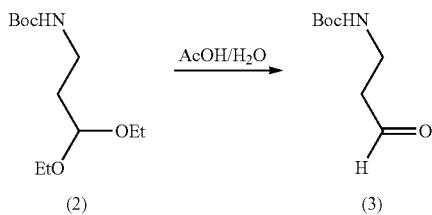 [SMILES: CCOC(CCNC(=O)OC(C)(C)C)OCC ; CC(C)(C)OC(=O)NCCC=O]

The protected amine (2) (3.27 g, 13.2 mmol) was diluted in a mixture of acetic acid (5.1 mL) and water (1.4 mL), and the solution was stirred for 16 h, at room temperature. The pH of the solution was then slowly brought up to 7 with solid sodium carbonate. Diethyl ether (15 mL) was then added, and the organic phase was washed with water (1×10 mL) and brine (1×10 mL). After separation, the organic phase was dried with anhydrous magnesium sulphate, filtered and concentrated under reduced pressure. The crude product was quickly purified by flash chromatography on silica gel (eluent: diethyl ether/pentane 4:6). The aldehyde was obtained as a yellow oil (530 mg, 23%). $^1$H NMR (300 MHz, CDCl$_3$) δ (ppm) 9.74 (s, 1H), 4.97 (s, 1H), 3.46 (t, 2H, J=7.0 Hz), 2.64 (t, 2H, J=7.0 Hz), 1.36 (s, 9H).

Step 3: Preparation of the Imine

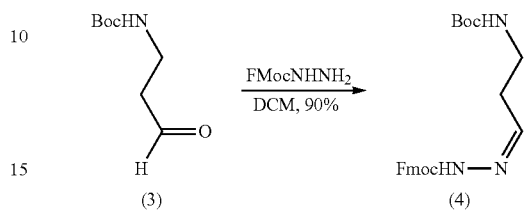

The aldehyde (3) (530 mg, 3.06 mmol) was diluted in dichloromethane (15 mL), and Fmoc-hydrazine (780 mg, 3.06 mmol) was added. The mixture was stirred for 16 h at room temperature. The solvent was removed under reduced pressure and the crude product was triturated in petroleum ether. The imine was obtained as a white powder (730 mg, 68%). $^1$H NMR (300 MHz, DMSO-d$_6$) δ (ppm) 7.87-7.27 (m, 8H), 6.83 (s, 1H), 4.36 (s, 2H), 4.22 (s, 1H), 3.29 (s, 2H), 2.23 (s, 2H), 1.32 (s, 9H). $^{13}$C NMR (75.5 MHz, CDCl$_3$) δ (ppm) 143.7, 141.3, 127.8, 127.1, 125.0, 120.0, 78.4, 67.0, 49.4, 47.2, 38.5, 28.4, 27.7. IR (CHCl$_3$) ν (cm$^{-1}$) 3344, 3255, 3064, 2976, 2927, 1708, 1683, 1531, 1446, 1365, 1248, 1170, 1029.

Step 4: Reduction of the Imine

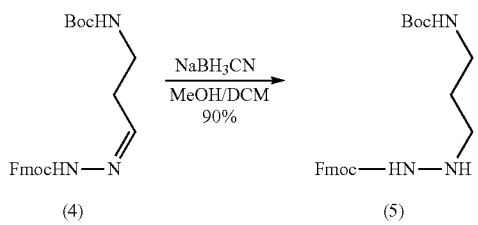

The imine (4) (730 mg, 1.78 mol) was dissolved in a mixture of dichloromethane (12 mL) and methanol (8 mL). Sodium cyanoborohydride (146 mg, 62.8 mmol) was added and the pH was slowly brought up to 4 with 2N HCl. The mixture was stirred for 45 minutes at room temperature, and then the pH was brought up to 7 with solid sodium bicarbonate. The mixture was filtered and concentrated under reduced pressure. The residue was dissolved in ethyl acetate (30 mL). The organic phase was washed with water (1×40 mL) and brine (1×40 mL), and then dried with anhydrous magnesium sulphate, filtered and concentrated under reduced pressure. The reduced imine was obtained as a white-orange solid (720 mg, 98%). $^1$H NMR (300 MHz, DMSO-d$_6$) δ (ppm) 7.86-7.26 (m, 8H), 4.29-4.20 (m, 2H), 4.20-4.12 (m, 1H), 2.89 (t, 2H, J=6.3 Hz), 2.70-2.52 (m, 2H), 1.43-1.34 (m, 2H), 1.33 (s, 9H). $^{13}$C NMR (75.5 MHz, CDCl$_3$) δ (ppm) 157.0, 156.4, 143.6, 141.3, 127.8, 127.1, 125.0, 120.0, 79.5, 67.3, 49.3, 47.1, 38.3, 28.4, 27.4. IR (CHCl$_3$) ν (cm$^{-1}$) 3318, 3064, 2976, 2937, 1700, 1520, 1478, 1450, 1390, 1365, 1273, 1252, 1171, 1040.

Step 5: Preparation of the Benzyl Ester

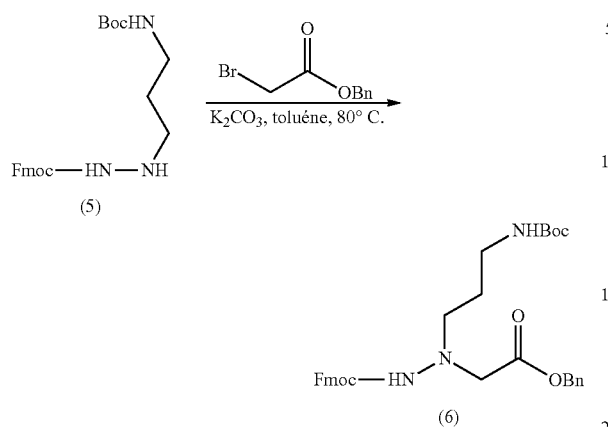

The reduced imine (5) (720 mg, 1.75 mmol) was dissolved in toluene (22 mL) and the mixture was heated to 80° C. Benzyl bromoacetate (521 mg, 2.28 mmol) and dried K$_2$CO$_3$ (170 mg, 1.23 mmol) were added, and the reaction was stirred for 24 h at 80° C. The mixture was filtered and washed with ethyl acetate (40 mL). The organic phase was washed with water (1×30 mL) and brine (1×30 mL) before it was dried with anhydrous sodium sulphate, filtered and concentrated under reduced pressure. The crude product was purified by flash chromatography on silica gel (eluent: petroleum ether/ethyl acetate 3:1). The benzylic ester was obtained as a yellow oil (300 mg, 31%). $^1$H NMR (300 MHz, CDCl$_3$) δ (ppm) 7.81-7.28 (m, 13H), 5.17 (s, 2H), 4.42 (d, 2H, J=7.2 Hz), 4.19 (s, 1H), 3.72 (s, 2H), 3.21 (s, 2H), 2.97 (s, 2H), 1.68-1.54 (m, 2H), 1.42 (s, 9H). $^{13}$C NMR (75.5 MHz, CDCl$_3$) δ (ppm) 169.5, 156.5, 155.9, 143.7, 141.4, 128.7, 128.6, 128.4, 127.7, 127.1, 126.0, 120.0, 119.8, 77.2, 66.7, 57.2, 54.2, 47.3, 44.5, 38.6, 28.4, 27.4. IR (CHCl$_3$) ν (cm$^{-1}$) 3350, 3064, 2972, 1739, 1729, 1693, 1682, 1609, 1503, 1453, 1390, 1365, 1248, 1171, 1107.

Step 6: Preparation of N,N-di-(tert-butoxycarbonyl)-guanidine as Described in Journal of Organic Chemistry, Vol. 63, No. 23, 1998

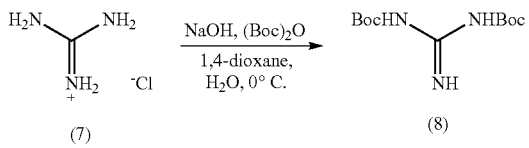

Guanidine chlorhydrate (7) (12.3 g, 128 mmol) and sodium hydroxide (20.8 g, 519 mmol) were dissolved in water (125 mL), and 1,4-dioxane (250 mL) were added. The mixture was cooled to 0° C. and di-tert-butyl-carbonate (62.9 g, 288 mmol) was added. The mixture was allowed to warm at room temperature within 16 h. The solution was concentrated in vacuo to one-third of its initial volume. Water (150 mL) was added to the resulting mixture, and the solution was extracted with ethyl acetate (3×80 mL). The organic phase was then washed with 10% citric acid (1×100 mL), water (1×100 mL) and brine (1×100 mL), dried with anhydrous magnesium sulfate, filtered and concentrated under reduced pressure. The crude product was purified by flash chromatography on silica gel (eluent: 100% dichloromethane to dichloromethane/methanol 95:5). The di-protected guanidine was obtained as a white powder (30.54 g, 91%). $^1$H NMR (300 MHz, DMSO-d$_6$) δ (ppm) 10.42 (s, 1H), 8.47 (s, 1H), 1.37 (s, 18H). $^{13}$C NMR (75.5 MHz, CDCl$_3$) δ (ppm) 158.3, 82.3, 28.1. IR (CHCl$_3$) ν (cm$^{-1}$) 3407, 3124, 2976, 2930, 1792, 1641, 1549, 1453, 1397, 1365, 1248, 1153.

Step 7: Preparation of N,N-di-Boc-N'-trifluoromethanesulfonylguanidine as Described in Journal of Organic Chemistry, Vol. 63, No. 23, 1998

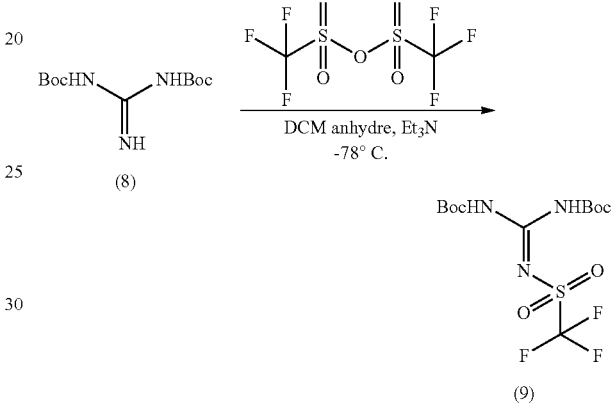

Under an inert atmosphere, N,N-di-(tert-butoxycarbonyl)-guanidine (8) (10 g, 38 mmol) was dissolved in anhydrous dichloromethane (200 mL). The mixture was cooled to −78° C., and triethylamine (5.65 mL, 40.5 mmol) was added. Trifluoromethanesulfonic anhydride (6.81 mL, 40.5 mmol) was added dropwise, over a 30-minute period. The reaction mixture was stirred for 16 h at room temperature. The solution was washed with 2M sodium bisulphate (1×200 mL) and water (1×200 mL), and the organic phase was dried with anhydrous sodium sulphate, filtered and concentrated. The crude product was purified by flash chromatography on silica gel (eluent: 100% dichloromethane) and recrystallized in hexanes. N,N-di-Boc-N'-trifluoromethanesulfonylguanidine was obtained as white crystals (11.74 g, 78%). $^1$H NMR (300 MHz, DMSO-d$_6$) δ (ppm) 1.43 (s, 18H). $^{13}$C NMR (75.5 MHz, CDCl$_3$) δ (ppm) 151.4, 121.4, 117.1, 86.0, 27.8. IR (CHCl$_3$) ν (cm$^{-1}$) 3304, 2983, 1785, 1736, 1626, 1556, 1464, 1376, 1340, 1259, 1192.

Step 8: Addition of Guanidine

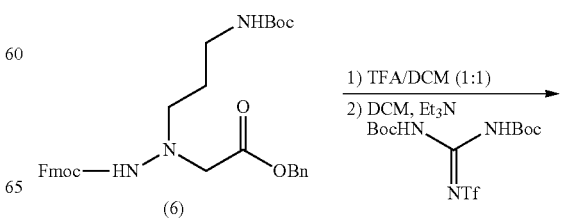

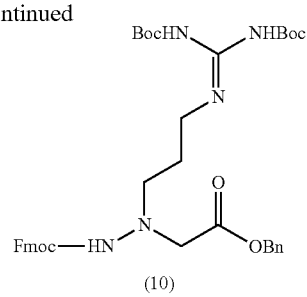

Benzylic ester (6) (300 mg, 0.54 mmol) was dissolved in dichloromethane (1.65 mL), trifluoroacetic acid (1.65 mL) was added. The mixture was stirred for 16 h at room temperature. Dichloromethane (15 mL) and water (5 mL) were added, and the pH was slowly brought up to 8 with solid sodium carbonate. After separation, the organic phase was washed with water (1×40 mL) and brine (1×40 mL), and then dried with anhydrous magnesium sulphate, filtered and concentrated under reduced pressure to the half of its volume. Triethylamine (82 µL) and N,N-di-Boc-N'-trifluoro methanesulfonylguanidine (9) (190 mg) were added and the mixture was stirred on 16 h. The solution was then washed with 2M sodium bisulphate (1×10 mL), a saturated solution of sodium bicarbonate (1×10 mL), water (1×15 mL) and brine (1×15 mL). The organic phase was dried with anhydrous sodium sulphate, filtered and concentrated. The crude product was purified by flash chromatography on silica gel (eluent: petroleum ether/ethyl acetate 7:3). The product (10) was obtained as a yellow oil (291 mg, 77%) $^1$H NMR (300 MHz, CDCl$_3$) δ (ppm) 7.76-7.11 (m, 13H), 5.16 (s, 2H), 4.41 (s, 2H), 4.21 (s, 1H), 3.79 (s, 2H), 3.54 (s, 2H), 2.98 (s, 2H), 1.70 (s, 2H), 1.48 (s, 18H). $^{13}$C NMR (75.5 MHz, CDCl$_3$) δ (ppm) 170.5, 163.6, 156.2, 153.2, 143.8, 141.3, 135.2, 128.7, 128.6, 128.4, 127.7, 127.1, 125.1, 121.4, 120.0, 83.0, 79.2, 66.6, 57.7, 53.6, 47.2, 38.5, 31.2, 28.3, 28.1, 27.1. IR (CHCl$_3$) v (cm$^{-1}$) 3329, 3146, 3064, 2980, 1715, 1612, 1453, 1411, 1160.

Step 9: Preparation of the Carboxylic Acid

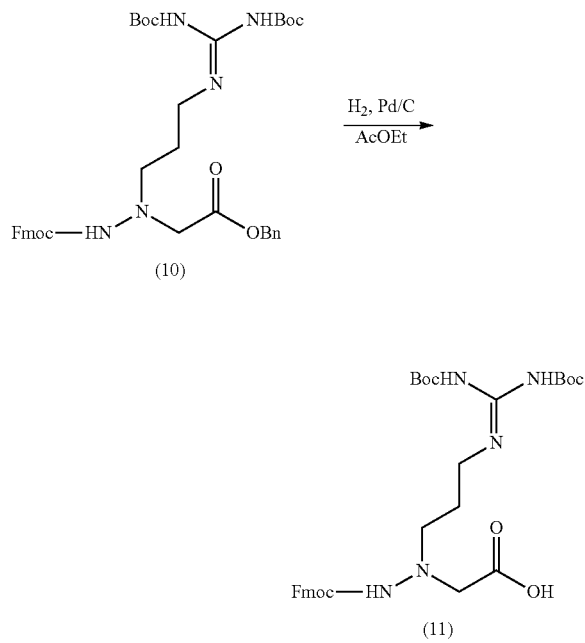

Benzylic ester (10) (291 mg, 0.41 mmol) was dissolved in ethyl acetate (6 mL). Palladium on activated carbon (19 mg) was added, and the reaction mixture was put under an hydrogen atmosphere. The solution mixture was stirred for 6 h, filtered on Celite®, rinsed with ethyl acetate (5×10 mL) and concentrated. Aza-β3-arginine was obtained as a white foam (240 mg, 94%). $^1$H NMR (300 MHz, CDCl$_3$) δ (ppm) 7.76-7.24 (m, 8H), 4.49 (s, 2H, J=7.4 Hz), 4.21 (t, 1H, J=6.9 Hz), 3.68 (s, 2H), 3.49 (s, 2H), 3.00 (s, 2H), 1.75 (s, 2H), 1.53-1.40 (m, 18H). $^{13}$C NMR (75.5 MHz, CDCl$_3$) δ (ppm) 172.8, 156.8, 156.2, 153.0, 143.6, 141.3, 127.7, 127.1, 125.1, 120.0, 83.7, 67.0, 58.8, 53.4, 47.2, 38.8, 28.2, 281, 27.1. IR (CHCl$_3$) v (cm$^{-1}$) 3329, 2979, 1722, 1623, 1474, 1453, 1421, 1231, 1150.

EXAMPLE 2

Synthesis of Amino Acid Aza-β3-leucine

Step 1: Preparation of Fmoc-hydrazine

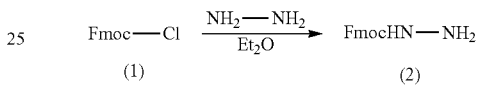

Hydrazine (18.0 mL, 213 mmol) was dissolved in diethyl ether (240 mL) at 0° C. A solution of Fmoc chloride (1) (12.0 g, 46.4 mmol) in diethyl ether (240 mL) was added to the hydrazine solution over a 30-minute period. The reaction mixture was stirred at room temperature for 16 h. The solution was evaporated, and water (400 mL) and ethyl acetate (400 mL) were added. The organic phase was washed with water (4×150 mL). The resulting suspension was evaporated. Fmoc-hydrazine (2) was obtained as a white solid (13.92 g, 118%). $^1$H NMR (300 MHz, CDCl$_3$) δ (ppm) 7.71-7.29 (m, 8H), 6.05 (s, 1H), 4.45 (d, 1H, J=6.8 Hz), 4.23 (t, 1H, J=8.3 Hz), 3.81 (s, 2H). $^{13}$C NMR (75.5 MHz, CDCl$_3$) δ (ppm) 143.6, 141.3, 127.8, 127.1, 120.1, 67.3, 47.1 IR (CHCl$_3$) v (cm$^{-1}$) 1686, 1633, 1506, 1446.

Step 2: Preparation of the Imine

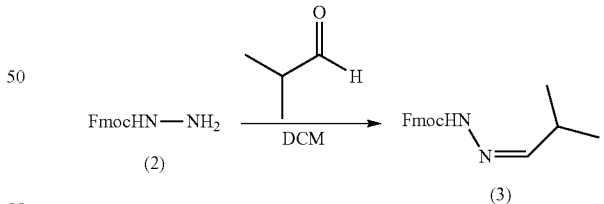

Fmoc-hydrazine (2) (3.66 g, 14.4 mmol) was dissolved in dichloromethane (55 mL), and isobutyraldehyde (1.31 mL, 14.4 mmol) was added. The mixture was stirred for 16 h and evaporated. The product (3) was obtained as a white powder (4.12 g, 93%). $^1$H NMR (300 MHz, CDCl$_3$) δ (ppm) 7.78-7.26 (m, 8H), 7.09 (d, 1Hm J=4.7 Hz), 4.51 (d, 2H, J=6.8 Hz), 4.29 (s, 1H), 2.64 (sext, 1H, J=4.1 Hz), 1.13 (d, 6H, J=5.9 Hz). $^{13}$C NMR (75.5 MHz, CDCl$_3$) δ (ppm) 143.7, 141.3, 127.8, 127.1, 125.2, 120.0, 67.2, 47.0, 31.4, 19.9. IR (CHCl$_3$) v (cm$^{-1}$) 3237, 3068, 1258, 2866, 1708, 1545, 1464, 1450, 1382, 1354, 1259, 1185.

Step 3: Imine Reduction

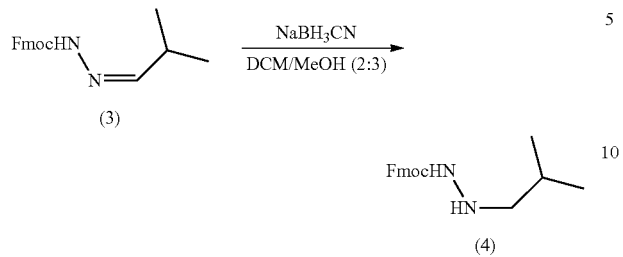

The imine (3) (4.12 g, 13.4 mmol) was dissolved in 70 mL of a mixture of dichloromethane and methanol (3:2). NaBH$_3$CN (1.01 g, 16.0 mmol) was added and the pH was brought up to 4 with 1N HCl. The reaction mixture was stirred for 30 minutes. The solution was acidified to pH 1 with 1N HCl, and stirred for 10 minutes. The pH was then brought up to 7 with solid sodium carbonate, and then evaporated. The residue was dissolved in ethyl acetate (50 mL), and the organic phase was washed with water (1×50 mL) and brine (1×50 mL). The organic phase was dried with sodium sulphate, filtered and evaporated. The crude product was purified with a flash chromatography on silica gel (eluent:ethyl acetate/hexanes 3:7). The reduced imine (4) was obtained as a white powder (4.63 g, 112%). $^1$H NMR (300 MHz, CDCl$_3$) δ (ppm) 7.81-7.21 (m, 8H), 4.45 (s, 2H), 4.22 (t, 1H, J=6.6 Hz), 2.90 (s, 2H), 1.97 (s, 1H), 0.98 (d, 6H, J=5.2 Hz). $^{13}$C NMR (75.5 MHz, CDCl$_3$) δ (ppm) 157.2, 143.7, 141.3, 127.8, 127.1, 125.0, 120.0, 67.0, 60.0, 47.2, 26.7, 20.5. IR (CHCl$_3$) ν (cm$^{-1}$) 3322, 3255, 3064, 2955, 2884, 1694, 1527, 1489, 1457, 1383, 1273, 1192.

Step 4: Addition of Glyoxylic Acid

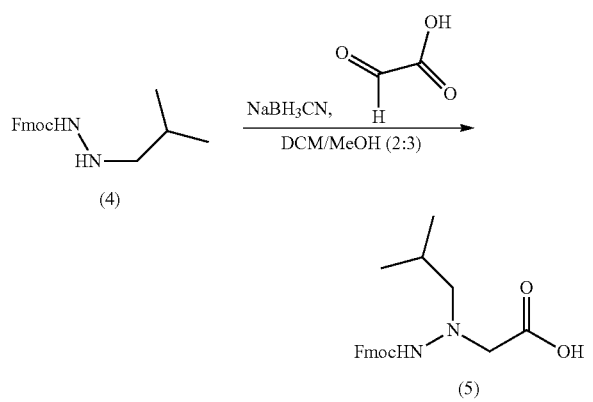

The reduced imine (4) (4.63 g, 14.9 mmol) was dissolved in 70 mL of a mixture of dichloromethane and methanol (3:2). Glyoxylic acid (1.65 g, 17.9 mmol) and NaBH$_3$CN (1.13 g, 17.9 mmol) were added. The pH was brought up to ph 4 with 1N HCl and stirred for 30 minutes, and the mixture was acidified to pH 1 for 10 minutes. The pH was then brought up to 4 with solid sodium carbonate. The reaction mixture was filtered and concentrated. The residue was dissolved in ethyl acetate (50 mL), and washed with water (1×50 mL) and brine (1×50 mL). The organic phase was dried with sodium sulphate, filtered and evaporated. Aza-β3-leucine (5) was obtained as a white solid foam (5.11 g, 93%). $^1$H NMR (300 MHz, CDCl$_3$) δ (ppm) 7.76-7.31 (m, 8H), 6.12 (s, 1H), 4.54 (d, 2H, J=6.2 Hz), 4.18 (s, 1H), 3.55 (s, 2H), 2.58 (d, 2H, J=7.0 Hz), 1.54 (s, 1H), 0.91 (d, 6H, J=6.5 Hz). $^{13}$C NMR (75.5 MHz, CDCl$_3$) δ (ppm) 171.2, 157.2, 143.4, 141.3, 127.8, 127.1, 124.9, 120.0, 67.1, 66.7, 60.5, 47.2, 26.3, 20.5. IR (CHCl$_3$) ν (cm$^{-1}$) 3251, 3051, 2958, 2869, 1739, 1514, 1451, 1364, 1254, 1147.

EXAMPLE 3

Synthesis of 4-amino-2-en-1-yl guanidine

Step 1: Preparation of 1-bromo-4-phthalimido-2-butene (1)

1,4-dibromo-2-butene (15.0 g, 70.1 mmol) was added to the stirred suspension of potassium phthalimide (4.32 g, 23.3 mmol) in DMF (24 mL). The mixture was stirred 48 h. Cooled water was added and the precipitated solid was filtered and dried at high vacuum to give the desired compound (1). The compound was purified with ethyl acetate/hexane 3:7 to give a white solid (4.28 g, 66%); $^1$H NMR (CDCl$_3$) δ (ppm) 3.92 (d, 2H, CH$_2$), 4.32 (d, 2H, CH$_2$), 5.89 (m, 2H, CH), 7.70-7.89 (m, 4H, Aromatic); $^{13}$C NMR (CDCl$_3$) δ (ppm) 168 (CO), 134 (CH), 132 (C aromatic), 129 (C aromatic), 128 (C aromatic), 123 (CH), 38 (CH$_2$N), 31 (CH$_2$Br).

Step 2: Preparation of N-(4-phthalimido-2-butenyl)hexamethylene tetrammonium bromide (2)

To a solution of 1-3 Hexamethylenetetramine (3.21 g, 22.9 mmol) in CHCl$_3$ (43 mL) was added dropwised a solution of 1-bromo-4-phthalimido-2-butene (1) (4.28 g, 15.3 mmol) in CHCl$_3$ (43 mL), The solution was stirred during 48 h. A white precipitate appeared. The solid was filtered and washed with chloroform. A white powder was obtained (6.91 g, 107% water trace, dried on high vacuum). $^1$H NMR (MeOD) δ (ppm) 3.45 (d, 2H, CH$_2$), 4.38 (d, 2H, CH$_2$), 4.50 (d, 6H, CH$_2$), 4.67 (d, 6H, CH$_2$), 5.85 (m, 1H, CH), 6.15 (m, 1H, CH), 7.80-7.89 (m, 4H, aromatic). $^{13}$C NMR (MeOD) δ (ppm) 168 (CO), 138 (C aromatic), 134 (C aromatic), 122 (CH), 117 (CH), 78 (CH$_2$), 70 (CH$_2$), 57 (CH$_2$N), 38 (CH$_2$Br).

Step 3: Preparation of N-(4-phthalimido-2-butenyl)ammonium chloride (3)

To a solution of compound (2) (4.32 g, 10.3 mmol) in ethanol (174 mL) was added dropwide a solution of concentrated HCl (7.25 mL, 12 M). The mixture was reflux during 2 h (around 90° C.). On cooling of the reaction mixture, the precipitate was filtered off and the filtrate was concentrated to give the desired product as a yellow oil (4.39 g). $^1$H NMR (MeOD) δ (ppm) 3.50 (d, 2H, CH$_2$), 4.28 (d, 2H, CH$_2$), 5.75 (m, 1H, CH), 5.95 (m, 1H, CH), 7.79-7.87 (m, 4H, aromatic). $^{13}$C NMR (MeOD) δ (ppm) 168 (CO), 134 (C aromatic), 132 (C aromatic), 131 (C aromatic), 124 (CH), 123 (CH), 40 (CH$_2$N), 38 (CH$_2$Br).

Step 4: Preparation of N-(4-phthalimido-2-butenyl) guanidine-(di-Boc) (4)

To a solution of triethylamine (1.05 mL), tert-butyl[N-(tert-butoxycarbonyl)-N'-(trifluoroacetyl)carbamimidoyl]

carbamate (6) (1.97 g, 5.03 mmol) in DCM (56 mL) was added compound (3) (1.4 g, 5.55 mmol). The solution was stirred overnight. DCM was added and the organic phase was washed with sodium bisulfate (2M), a saturated solution of NaHCO$_3$ and brine. The organic phase was dried with magnesium sulfate, filtered and concentrated. The crude compound was purified with ethyl acetate/hexane (30/70) to (40/60). Rf=0.58. A white solid was obtained (2.13 g, 93%). $^1$H NMR (CDCl$_3$) δ (ppm) 1.48 (s, 18H, CH$_3$), 4.05 (m, 2H, CH$_2$), 4.28 (d, 2H, CH$_2$), 5.30 (m, 2H, CH), 7.73-7.84 (m, 4H, aromatic), 8.45 (sl, 1H, NH), 11.48 (s, 1H, NH). $^{13}$C NMR (CDCl$_3$) δ (ppm) 133 (C aromatic), 132 (C aromatic), 129 (C aromatic), 126 (CH), 123 (CH), 41 (CH$_2$), 38 (CH$_2$), 28 (CH$_3$ boc).

Step 5: Preparation of N-(2-butenyl) guanidine-(di-Boc) (5)

To a solution of compound (4) (1.86 g, 4.06 mmol) in methanol (12.01 mL) and chloroform (9.5 mL) was added hydrazine (1.0 mL). The solution was stirred during 4 h. A white solid appeared during the reaction. The solid was filtered and the filtrate was diluted with chloroform. The organic phase was washed with sodium hydroxide (1M). The organic phase was dried with magnesium sulfate, filtered and concentrated. We obtained a yellow solid (1.22 g, 92%). $^1$H NMR (CDCl$_3$) δ (ppm) 1.49 (s, 18H, CH$_3$), 3.30 (d, 2H, CH$_2$), 4.06 (d, 2H, CH$_2$), 5.65-5.76 (m, 2H, CH), 8.34 (s, 1H, NH), 11.51 (s, 1H, NH). $^{13}$C NMR (CDCl$_3$) δ (ppm) 163 (CO), 155 (CO), 153 (C), 134, 128, 125, 83, 79, 43 (CH$_2$), 28 (CH$_3$ boc).

EXAMPLE 4

Synthesis of Aza-β3-lysine Amino Acid

Step 1: Preparation of tert-butyl N-(4,4-diethoxybutyl)carbamate (1)

In a flask were added 4,4-diethoxybutan-1-amine (2 g, 12.4 mmol), triethylamine (1.8 mL, 12.9 mmol) and DCM (10 mL). The solution was cooled to 0° C. To this solution was added dropwised a solution of Boc$_2$O (2.7 g, 12.4 mmol) in DCM (10 mL). The solution was stirred overnight then evaporated. The compound was purified by flash chromatography by using ethyl acetate/hexane (10/90) to (30/70) to give (0.72 g, 89%). $^1$H NMR (CDCl$_3$) δ (ppm) 1.17 (t, 6H, CH$_3$), 1.43 (s, 9H, CH$_3$), 1.55 (m, 4H, CH$_2$), 3.12 (d, 2H, CH$_2$), 3.45 (m, 2H, CH$_2$), 3.47 (m, 2H, CH$_2$), 4.47 (t, 1H, CH), 4.64 (s, 1H, NH).

Step 2: Preparation of N-t-butyloxycarbonyl-4-amino-butanal (2)

A solution of 1-Boc-amino-3,3-diethoxypropane (15.3 g, 58.5 mmol) in AcOH (27 mL) and water (8 mL) was stirred at room temperature for 10 h, neutralized with Na$_2$CO$_3$, taken up in ether, and washed with water and brine. The organic phase was evaporated under vacuum to give a yellow oil used as such in the next step (14.25 g). $^1$H NMR (400 MHz, CDCl$_3$) δ (ppm) 1.47 (s, CH$_3$ boc), 1.90 (m), 3.47 (m), 3.51 (q), 5.30 (s).

Step 3: Preparation of Fmoc-NHN=CH(CH$_2$)$_2$NH-Boc (3)

Fmoc carbazate (14.86 g, 58.4 mmol) was added to a stirred solution of the aldehyde (2) (10.95 g, 58.5 mmol) (261 mL) The reaction mixture was stirred for 12 h at 45° C. and concentrated under vacuum to give crude solid that was triturated with petroleum ether to afford the hydrazone as a white solid (24.38 g). $^1$H NMR (400 MHz, CDCl$_3$) δ (ppm) 1.35 (s, 9H, CH$_3$ boc), 1.70 (m, 2H, CH$_2$), 2.10 (m, 2H, CH$_2$), 2.90 (m, 2H, CH$_2$), 4.20 (m, 1H, CH), 6.83 (sl, 1H, NH), 7.65 (d, CH aromatic), 7.85 (d, CH aromatic), 8.66 (sl, 1H, NH), 10.70 (sl, 1H, NH).

Step 4: Preparation of FmocNHN=CH(CH$_2$)$_2$NHBoc (4)

Then, Fmoc protected hydrazone (3) (24.38 g, 58.4 mmol) was dissolved in a mixture DCM/MeOH (166/100 mL) and was added NaBH$_3$CN (4.44 g, 70.7 mmol). The pH was adjusted at pH 3-4 with HCl (2N) (Keep the pH at 3-4 during 1 h). The solution was neutralized with NaHCO$_3$ (pH 7-8). The solvent was concentrated under vacuum. Ethyl acetate was added and the organic phase was washed with water, brine and dried with magnesium sulfate. The organic phase was filtered and concentrated then purified by flash chromatography by using dichloromethane/ethyl acetate 60/40 to give oil (4.46 g, 18%). $^1$H NMR (400 MHz, CDCl$_3$) δ (ppm) 1.35 (s, 9H, CH$_3$ boc), 2.62 (m, 2H, CH$_2$), 3.12 (m, 2H, CH$_2$), 3.78 (m, 2H, CH$_2$), 6.05 (sl, 1H, NH), 6.36 (sl, 1H, NH), 7.27 (t, 1H, CH), 7.30 (t, 1H, CH), 7.65 (d, 1H, CH), 7.85 (d, 1H, CH).

Step 5: Preparation of FmocNHN(CH$_2$—COOH)—CH(CH$_2$)$_2$NHBoc (5)

To a solution of compound (2) (4.4 g, 10.50 mmol), glyoxylic acid (1.83 g, 19.88 mmol) in a mixture of MeOH/DCM (60/30) was added NaBH$_3$CN (1.24 g, 19.73 mmol). The pH was controlled between 3-4 by addition of HCl (2N) during one hour. The solution was filtrated and concentrated. Ethyl acetate was added and the organic phase was washed with water and brine. The organic phase dried with magnesium sulfate and concentrated under vacuum to give the crude compound. The product was purified by flash chromatography (Ether (95)/MeOH (5)/AcOH (0.25) to give a white solid (4.1 g, 82%). $^1$H NMR (400 MHz, CDCl$_3$) δ (ppm) 1.35 (s, 9H, CH$_3$ boc), 2.62 (m, 2H, CH$_2$), 3.12 (m, 2H, CH$_2$), 3.78 (m, 2H, CH$_2$), 6.05 (sl, 1H, NH), 7.27 (t, 1H, CH), 7.30 (t, 1H, CH), 7.65 (d, 1H, CH), 7.85 (d, 1H, CH).

EXAMPLE II

Cell Cycle Analysis

To perform cell cycle analysis on LNCaP, 4×10$^5$ cells are seeded in 10 cm culture dish and grown for 24 hours without treatment. Cells are then treated with vehicle (0.1% DMSO) or with 100 μM or 200 μM of peptides Ac-LLLLRVKR-NH$_2$ or Ac-[D-Leu]LLLRVKR-NH$_2$. Treatments are carried out in complete medium (10% FBS) for a period of 96 hours and cell media is changed every 24 hours to offset peptide degradation. Cells are harvested using trypsin, washed once with PBS, resuspended in 0.5 mL PBS and fixed by drop wise addition of 1.5 mL of ice-cold ethanol. After a 30 minutes incubation at room temperature, cells are washed with PBS and DNA staining is performed in 20 mM HEPES pH 7.2, 0.16M NaCl, 1 mM EGTA buffer containing 10 μg/mL of RNAseA and 10 μg/mL of propidium iodine.

Flow cytometry is performed using a FACScan™ cytometer (Becton Dickinson, Mountain View, Calif.) equipped with a 15 mW argon ion laser tuned at 488 nm. A minimum of 10 000 gated events by sample are acquired. Forward and side scatter signals are used to establish the live gate to exclude debris and cell clumps and a second live gate is set using the FL3-A and FL3-W parameters of the doublet discrimination module (DDM), allowing single cell measurements. The percentages of cells in different phases of cell cycle are calculated by ModFit software (Verity Software House, Topsham, Me.).

While the invention has been described in connection with specific embodiments thereof, it will be understood that it is capable of further modifications and this application is intended to cover any variations, uses, or adaptations of the invention, and including such departures from the present disclosure as come within known or customary practice within the art to which the invention pertains and as may be applied to the essential features hereinbefore set forth, and as follows in the scope of the appended claims.

What is claimed is:

1. A peptide sequence comprising the following formula:

[D-Leu]-LLLRVK-[AMBA].

2. A composition comprising the peptide of claim 1 and a carrier.

3. The composition of claim 2, for treating cancer.

4. The composition of claim 2, further comprising at least one anti-cancer drug.

5. The composition of claim 2, formulated for a concurrent administration with at least one anti-cancer drug.

6. The composition of claim 3, wherein the cancer is breast cancer, glioma, large intestinal cancer, lung cancer, small cell lung cancer, stomach cancer, liver cancer, blood cancer, bone cancer, pancreatic cancer, skin cancer, head or neck cancer, cutaneous or intraocular melanoma, uterine sarcoma, ovarian cancer, rectal or colorectal cancer, anal cancer, colon cancer, fallopian tube carcinoma, endometrial carcinoma, cervical cancer, vulval cancer, squamous cell carcinoma, vaginal carcinoma, Hodgkin's disease, non-Hodgkin's lymphoma, esophageal cancer, small intestine cancer, endocrine cancer, thyroid cancer, parathyroid cancer, adrenal cancer, soft tissue tumor, urethral cancer, penile cancer, prostate cancer, chronic or acute leukemia, lymphocytic lymphoma, bladder cancer, kidney cancer, ureter cancer, renal cell carcinoma, renal pelvic carcinoma, CNS tumor, glioma, astrocytoma, glioblastoma multiforme, primary CNS lymphoma, bone marrow tumor, brain stem nerve gliomas, pituitary adenoma, uveal melanoma, testicular cancer, oral cancer, pharyngeal cancer, pediatric neoplasms, leukemia, neuroblastoma, retinoblastoma, glioma, rhabdomyoblastoma or sarcoma.

7. The composition of claim 2, wherein the composition is formulated for concurrent administration during a suitable anti-cancer therapy.

8. The composition of claim 7, wherein the anti-cancer therapy is at least one of a surgical procedure, chemotherapy, hormonal therapy and localization radiation.

9. The composition of claim 2, wherein the composition reduces cell proliferation, tumor growth or metastasis formation.

10. A method for the treatment of a cancer in a subject, comprising administering the peptide of claim 1 or the composition of claim 2 to the subject, thereby treating cancer in the subject.

11. The method of claim 10, wherein the cancer is breast cancer, glioma, large intestinal cancer, lung cancer, small cell lung cancer, stomach cancer, liver cancer, blood cancer, bone cancer, pancreatic cancer, skin cancer, head or neck cancer, cutaneous or intraocular melanoma, uterine sarcoma, ovarian cancer, rectal or colorectal cancer, anal cancer, colon cancer, fallopian tube carcinoma, endometrial carcinoma, cervical cancer, vulval cancer, squamous cell carcinoma, vaginal carcinoma, Hodgkin's disease, non-Hodgkin's lymphoma, esophageal cancer, small intestine cancer, endocrine cancer, thyroid cancer, parathyroid cancer, adrenal cancer, soft tissue tumor, urethral cancer, penile cancer, prostate cancer, chronic or acute leukemia, lymphocytic lymphoma, bladder cancer, kidney cancer, ureter cancer, renal cell carcinoma, renal pelvic carcinoma, CNS tumor, glioma, astrocytoma, glioblastoma multiforme, primary CNS lymphoma, bone marrow tumor, brain stem nerve gliomas, pituitary adenoma, uveal melanoma, testicular cancer, oral cancer, pharyngeal cancer, pediatric neoplasms, leukemia, neuroblastoma, retinoblastoma, glioma, rhabdomyoblastoma or sarcoma.

* * * * *

SEQUENCE LISTING

```
<160> NUMBER OF SEQ ID NOS: 31

<210> SEQ ID NO 1
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: At least one of acetyl, azido and PEG group,
      fatty acids, steroids derivatives and sugars linked to the
      N-terminal of the peptide sequence
<220> FEATURE:
<221> NAME/KEY: MISC_FEATURE
<222> LOCATION: (2)..(2)
<223> OTHER INFORMATION: Serine, an analogue or stereoisomer; not
      aromatic or negatively charged
<220> FEATURE:
<221> NAME/KEY: MISC_FEATURE
<222> LOCATION: (3)..(3)
<223> OTHER INFORMATION: Arginine, an analogue or stereoisomer; not
      aromatic or negatively charged
<220> FEATURE:
<221> NAME/KEY: MISC_FEATURE
<222> LOCATION: (4)..(4)
<223> OTHER INFORMATION: Histidine, an analogue or stereoisomer; not
      aromatic or negatively charged
<220> FEATURE:
<221> NAME/KEY: MISC_FEATURE
<222> LOCATION: (5)..(5)
<223> OTHER INFORMATION: Leucine, an analogue or stereoisomer; not
      aromatic or negatively charged
<220> FEATURE:
<221> NAME/KEY: MISC_FEATURE
<222> LOCATION: (7)..(7)
<223> OTHER INFORMATION: Any amino acid, an analogue or stereoisomer
<220> FEATURE:
<221> NAME/KEY: MISC_FEATURE
<222> LOCATION: (8)..(8)
<223> OTHER INFORMATION: A basic amino acid, an analogue or stereoisomer
<220> FEATURE:
<221> NAME/KEY: MISC_FEATURE
<222> LOCATION: (10)..(10)
<223> OTHER INFORMATION: Absent or arginine, an analogue or stereoisomer

<400> SEQUENCE: 1

Glx Xaa Xaa Xaa Xaa Arg Xaa Xaa Arg Xaa
1               5                   10

<210> SEQ ID NO 2
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Acetylated N-terminus
```

```
<220> FEATURE:
<221> NAME/KEY: MISC_FEATURE
<222> LOCATION: (8)..(8)
<223> OTHER INFORMATION: D-Arginine
<220> FEATURE:
<221> NAME/KEY: MISC_FEATURE
<222> LOCATION: (8)..(8)
<223> OTHER INFORMATION: Amidated C-terminus

<400> SEQUENCE: 2

Leu Leu Leu Leu Arg Val Lys Arg
1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Fluorescein thiourea
<220> FEATURE:
<221> NAME/KEY: MISC_FEATURE
<222> LOCATION: (1)..(1)
<223> OTHER INFORMATION: Beta-alanine
<220> FEATURE:
<221> NAME/KEY: MISC_FEATURE
<222> LOCATION: (9)..(9)
<223> OTHER INFORMATION: Amidated C-terminus

<400> SEQUENCE: 3

Ala Leu Leu Leu Arg Val Lys Arg
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Fluorescein thiourea
<220> FEATURE:
<221> NAME/KEY: MISC_FEATURE
<222> LOCATION: (1)..(1)
<223> OTHER INFORMATION: PEG-8
<220> FEATURE:
<221> NAME/KEY: MISC_FEATURE
<222> LOCATION: (8)..(8)
<223> OTHER INFORMATION: Amidated C-terminus

<400> SEQUENCE: 4

Leu Leu Leu Leu Arg Val Lys Arg
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Fluorescein thiourea
<220> FEATURE:
<221> NAME/KEY: MISC_FEATURE
<222> LOCATION: (1)..(1)
<223> OTHER INFORMATION: 8-aminooctanoic aicd
```

```
<220> FEATURE:
<221> NAME/KEY: MISC_FEATURE
<222> LOCATION: (8)..(8)
<223> OTHER INFORMATION: Amidated C-terminus

<400> SEQUENCE: 5

Leu Leu Leu Leu Arg Val Lys Arg
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Acetylated N-terminus
<220> FEATURE:
<221> NAME/KEY: MISC_FEATURE
<222> LOCATION: (8)..(8)
<223> OTHER INFORMATION: Amidated C-terminus

<400> SEQUENCE: 6

Leu Leu Leu Leu Arg Val Lys Arg
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Acetylated N-terminus
<220> FEATURE:
<221> NAME/KEY: MISC_FEATURE
<222> LOCATION: (1)..(1)
<223> OTHER INFORMATION: D-Leucine
<220> FEATURE:
<221> NAME/KEY: MISC_FEATURE
<222> LOCATION: (9)..(9)
<223> OTHER INFORMATION: Amidated C-terminus

<400> SEQUENCE: 7

Leu Leu Leu Leu Leu Arg Val Lys Arg
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (8)..(8)
<223> OTHER INFORMATION: Amidated C-terminus

<400> SEQUENCE: 8

Leu Leu Leu Leu Arg Val Lys Arg
1               5

<210> SEQ ID NO 9
<211> LENGTH: 7
<212> TYPE: PRT
<213> ORGANISM: Artificial Sequence
<220> FEATURE:
```

```
<223> OTHER INFORMATION: Synthetic Peptide
<220> FEATURE:
<221> NAME/KEY: MISC_FEATURE
<222> LOCATION: (1)..(1)
<223> OTHER INFORMATION: Acetylated N-terminus
<220> FEATURE:
<221> NAME/KEY: MISC_FEATURE
<222> LOCATION: (7)..(7)
<223> OTHER INFORMATION: Labeled with bombesin analogue tracer AMBA

<400> SEQUENCE: 9

Leu Leu Leu Leu Arg Val Lys
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Acetylated N-terminus
<220> FEATURE:
<221> NAME/KEY: MISC_FEATURE
<222> LOCATION: (4)..(4)
<223> OTHER INFORMATION: Norleucine
<220> FEATURE:
<221> NAME/KEY: MISC_FEATURE
<222> LOCATION: (8)..(8)
<223> OTHER INFORMATION: Amidated C-terminus

<400> SEQUENCE: 10

Leu Leu Leu Leu Arg Val Lys Arg
1               5

<210> SEQ ID NO 11
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Acetylated N-terminus
<220> FEATURE:
<221> NAME/KEY: MISC_FEATURE
<222> LOCATION: (1)..(1)
<223> OTHER INFORMATION: Norleucine
<220> FEATURE:
<221> NAME/KEY: MISC_FEATURE
<222> LOCATION: (2)..(2)
<223> OTHER INFORMATION: Norleucine
<220> FEATURE:
<221> NAME/KEY: MISC_FEATURE
<222> LOCATION: (3)..(3)
<223> OTHER INFORMATION: Norleucine
<220> FEATURE:
<221> NAME/KEY: MISC_FEATURE
<222> LOCATION: (4)..(4)
<223> OTHER INFORMATION: Norleucine
<220> FEATURE:
<221> NAME/KEY: MISC_FEATURE
<222> LOCATION: (8)..(8)
<223> OTHER INFORMATION: Amidated C-terminus

<400> SEQUENCE: 11

Leu Leu Leu Leu Arg Val Lys Arg
1               5

<210> SEQ ID NO 12
```

```
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Acetylated N-terminus
<220> FEATURE:
<221> NAME/KEY: MISC_FEATURE
<222> LOCATION: (1)..(1)
<223> OTHER INFORMATION: Norleucine
<220> FEATURE:
<221> NAME/KEY: MISC_FEATURE
<222> LOCATION: (8)..(8)
<223> OTHER INFORMATION: Amidated C-terminus

<400> SEQUENCE: 12

Leu Leu Leu Leu Arg Val Lys Arg
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Acetylated N-terminus
<220> FEATURE:
<221> NAME/KEY: MISC_FEATURE
<222> LOCATION: (1)..(1)
<223> OTHER INFORMATION: Norleucine
<220> FEATURE:
<221> NAME/KEY: MISC_FEATURE
<222> LOCATION: (2)..(2)
<223> OTHER INFORMATION: Norleucine
<220> FEATURE:
<221> NAME/KEY: MISC_FEATURE
<222> LOCATION: (4)..(4)
<223> OTHER INFORMATION: Norleucine

<400> SEQUENCE: 13

Leu Leu Leu Leu Arg Val Lys Arg
1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Acetylated N-terminus
<220> FEATURE:
<221> NAME/KEY: MISC_FEATURE
<222> LOCATION: (1)..(2)
<223> OTHER INFORMATION: Pseudo peptide bond "click"
<220> FEATURE:
<221> NAME/KEY: MISC_FEATURE
<222> LOCATION: (8)..(8)
<223> OTHER INFORMATION: Amidated C-terminus

<400> SEQUENCE: 14

Leu Leu Leu Leu Arg Val Lys Arg
1               5

<210> SEQ ID NO 15
```

```
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Acetylated N-terminus
<220> FEATURE:
<221> NAME/KEY: MISC_FEATURE
<222> LOCATION: (2)..(3)
<223> OTHER INFORMATION: Pseudo peptide bond "click"
<220> FEATURE:
<221> NAME/KEY: MISC_FEATURE
<222> LOCATION: (8)..(8)
<223> OTHER INFORMATION: Amidated C-terminus

<400> SEQUENCE: 15

Leu Leu Leu Leu Arg Val Lys Arg
1               5

<210> SEQ ID NO 16
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Acetylated N-terminus
<220> FEATURE:
<221> NAME/KEY: MISC_FEATURE
<222> LOCATION: (1)..(2)
<223> OTHER INFORMATION: Pseudo peptide bond, double bond
<220> FEATURE:
<221> NAME/KEY: MISC_FEATURE
<222> LOCATION: (8)..(8)
<223> OTHER INFORMATION: Amidated C-terminus

<400> SEQUENCE: 16

Leu Leu Leu Leu Arg Val Lys Arg
1               5

<210> SEQ ID NO 17
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Acetylated N-terminus
<220> FEATURE:
<221> NAME/KEY: MISC_FEATURE
<222> LOCATION: (8)..(8)
<223> OTHER INFORMATION: Delta-R-COO

<400> SEQUENCE: 17

Leu Leu Leu Leu Arg Val Lys Arg
1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
```

```
<223> OTHER INFORMATION: Acetylated N-terminus
<220> FEATURE:
<221> NAME/KEY: MISC_FEATURE
<222> LOCATION: (8)..(8)
<223> OTHER INFORMATION: Aminated C-terminus

<400> SEQUENCE: 18

Leu Leu Leu Ser Arg Val Lys Arg
1               5

<210> SEQ ID NO 19
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Acetylated N-terminus
<220> FEATURE:
<221> NAME/KEY: MISC_FEATURE
<222> LOCATION: (1)..(1)
<223> OTHER INFORMATION: HN-PEG8 tagged
<220> FEATURE:
<221> NAME/KEY: MISC_FEATURE
<222> LOCATION: (8)..(8)
<223> OTHER INFORMATION: Aminated C-terminus

<400> SEQUENCE: 19

Leu Leu Leu Leu Arg Val Lys Arg
1               5

<210> SEQ ID NO 20
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Acetylated N-terminus
<220> FEATURE:
<221> NAME/KEY: MISC_FEATURE
<222> LOCATION: (1)..(1)
<223> OTHER INFORMATION: Aza-beta3 Leucine
<220> FEATURE:
<221> NAME/KEY: MISC_FEATURE
<222> LOCATION: (8)..(8)
<223> OTHER INFORMATION: Aminated C-terminus

<400> SEQUENCE: 20

Leu Leu Leu Leu Arg Val Lys Arg
1               5

<210> SEQ ID NO 21
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Acetylated N-terminus
<220> FEATURE:
<221> NAME/KEY: MISC_FEATURE
<222> LOCATION: (1)..(1)
<223> OTHER INFORMATION: Aza beta 3 Leucine
<220> FEATURE:
<221> NAME/KEY: MISC_FEATURE
<222> LOCATION: (8)..(8)
```

<223> OTHER INFORMATION: Delta R COO

<400> SEQUENCE: 21

Leu Leu Leu Leu Arg Val Lys Arg
1               5

<210> SEQ ID NO 22
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Acetylated N-terminus
<220> FEATURE:
<221> NAME/KEY: MISC_FEATURE
<222> LOCATION: (2)..(2)
<223> OTHER INFORMATION: Aza Beta 3 Leucine
<220> FEATURE:
<221> NAME/KEY: MISC_FEATURE
<222> LOCATION: (8)..(8)
<223> OTHER INFORMATION: Aminated C-terminus

<400> SEQUENCE: 22

Leu Leu Leu Leu Arg Val Lys Arg
1               5

<210> SEQ ID NO 23
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Acetylated N-terminus
<220> FEATURE:
<221> NAME/KEY: MISC_FEATURE
<222> LOCATION: (3)..(3)
<223> OTHER INFORMATION: Aza Beta 3 Leucine
<220> FEATURE:
<221> NAME/KEY: MISC_FEATURE
<222> LOCATION: (8)..(8)
<223> OTHER INFORMATION: Amidated C-terminus

<400> SEQUENCE: 23

Leu Leu Leu Leu Arg Val Lys Arg
1               5

<210> SEQ ID NO 24
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Acetylated N-terminus
<220> FEATURE:
<221> NAME/KEY: MISC_FEATURE
<222> LOCATION: (4)..(4)
<223> OTHER INFORMATION: Aza Beta 3 Leucine
<220> FEATURE:
<221> NAME/KEY: MISC_FEATURE
<222> LOCATION: (8)..(8)
<223> OTHER INFORMATION: Amidated C-terminus

<400> SEQUENCE: 24

Leu Leu Leu Leu Arg Val Lys Arg
1               5

<210> SEQ ID NO 25
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Acetylated N-terminus
<220> FEATURE:
<221> NAME/KEY: MISC_FEATURE
<222> LOCATION: (8)..(8)
<223> OTHER INFORMATION: Aza Beta 3 Arginine
<220> FEATURE:
<221> NAME/KEY: MISC_FEATURE
<222> LOCATION: (8)..(8)
<223> OTHER INFORMATION: Amidated C-terminus

<400> SEQUENCE: 25

Leu Leu Leu Leu Arg Val Lys Arg
1               5

<210> SEQ ID NO 26
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Acetylated N-terminus
<220> FEATURE:
<221> NAME/KEY: MISC_FEATURE
<222> LOCATION: (1)..(1)
<223> OTHER INFORMATION: D-Leucine
<220> FEATURE:
<221> NAME/KEY: MISC_FEATURE
<222> LOCATION: (7)..(7)
<223> OTHER INFORMATION: Labeled with bombesin analogue tracer AMBA

<400> SEQUENCE: 26

Leu Leu Leu Leu Arg Val Lys
1               5

<210> SEQ ID NO 27
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Acetylated N-terminus
<220> FEATURE:
<221> NAME/KEY: MISC_FEATURE
<222> LOCATION: (1)..(1)
<223> OTHER INFORMATION: Aza Beta 3 Leucine
<220> FEATURE:
<221> NAME/KEY: MISC_FEATURE
<222> LOCATION: (7)..(7)
<223> OTHER INFORMATION: Delta R-COO tagged

<400> SEQUENCE: 27

Leu Leu Leu Leu Arg Val Lys
1               5

```
<210> SEQ ID NO 28
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Acetylated N-terminus
<220> FEATURE:
<221> NAME/KEY: MISC_FEATURE
<222> LOCATION: (1)..(1)
<223> OTHER INFORMATION: PEG8 tag
<220> FEATURE:
<221> NAME/KEY: MISC_FEATURE
<222> LOCATION: (1)..(1)
<223> OTHER INFORMATION: D-Leucine
<220> FEATURE:
<221> NAME/KEY: MISC_FEATURE
<222> LOCATION: (7)..(7)
<223> OTHER INFORMATION: Labeled with bombesin analogue tracer AMBA

<400> SEQUENCE: 28

Leu Leu Leu Leu Arg Val Lys
1               5

<210> SEQ ID NO 29
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Acetylated N-terminus
<220> FEATURE:
<221> NAME/KEY: MISC_FEATURE
<222> LOCATION: (3)..(4)
<223> OTHER INFORMATION: Pseudo peptide bond "click"
<220> FEATURE:
<221> NAME/KEY: MISC_FEATURE
<222> LOCATION: (8)..(8)
<223> OTHER INFORMATION: Amidated C-terminus

<400> SEQUENCE: 29

Leu Leu Leu Leu Arg Val Lys Arg
1               5

<210> SEQ ID NO 30
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Acetylated N-terminus
<220> FEATURE:
<221> NAME/KEY: MISC_FEATURE
<222> LOCATION: (1)..(2)
<223> OTHER INFORMATION: Pseudo peptide bond "click"
<220> FEATURE:
<221> NAME/KEY: MISC_FEATURE
<222> LOCATION: (3)..(4)
<223> OTHER INFORMATION: Pseudo peptide bond "click"
<220> FEATURE:
<221> NAME/KEY: MISC_FEATURE
<222> LOCATION: (8)..(8)
<223> OTHER INFORMATION: Amidated C-terminus

<400> SEQUENCE: 30
```

```
Leu Leu Leu Leu Arg Val Lys Arg
1               5

<210> SEQ ID NO 31
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Acetylated N-terminus
<220> FEATURE:
<221> NAME/KEY: MISC_FEATURE
<222> LOCATION: (1)..(1)
<223> OTHER INFORMATION: PEG8 tag
<220> FEATURE:
<221> NAME/KEY: MISC_FEATURE
<222> LOCATION: (8)..(8)
<223> OTHER INFORMATION: Labeled with bombesin analogue tracer AMBA

<400> SEQUENCE: 31

Leu Leu Leu Leu Arg Val Lys Arg
1               5
```